United States Patent
Wang et al.

(10) Patent No.: US 10,234,694 B2
(45) Date of Patent: Mar. 19, 2019

(54) SPECTRALLY ENCODED PROBES

(71) Applicant: Canon U.S.A., Inc., Melville, NY (US)

(72) Inventors: Zhuo Wang, Middleton, MA (US); Seiji Takeuchi, Newton, MA (US)

(73) Assignee: Canon U.S.A., Inc., Melville, NY (US)

( * ) Notice: Subject to any disclaimer, the term of this patent is extended or adjusted under 35 U.S.C. 154(b) by 0 days.

(21) Appl. No.: 15/649,310

(22) Filed: Jul. 13, 2017

(65) Prior Publication Data
US 2018/0017806 A1  Jan. 18, 2018

Related U.S. Application Data

(60) Provisional application No. 62/363,089, filed on Jul. 15, 2016.

(51) Int. Cl.
| | | |
|---|---|---|
| *G01J 3/28* | (2006.01) | |
| *G02B 27/42* | (2006.01) | |
| *G01B 9/02* | (2006.01) | |
| *G01J 3/02* | (2006.01) | |
| *G01J 3/18* | (2006.01) | |

(Continued)

(52) U.S. Cl.
CPC ........ *G02B 27/425* (2013.01); *A61B 1/00096* (2013.01); *A61B 5/0062* (2013.01); *A61B 5/0084* (2013.01); *G01B 9/02044* (2013.01); *G01J 3/02* (2013.01); *G01J 3/0218* (2013.01); *G01J 3/18* (2013.01); *G02B 5/1866* (2013.01);
(Continued)

(58) Field of Classification Search
CPC ........ G01J 3/28; G01J 3/44; G01J 3/02; G01J 3/00; G01J 3/18; G02B 27/42; G02B 23/26; G02B 23/24; G02B 5/18; G01B 9/02

See application file for complete search history.

(56) References Cited

U.S. PATENT DOCUMENTS

| | | |
|---|---|---|
| 3,976,360 A | 8/1976 | Schroder |
| 4,074,306 A | 2/1978 | Kakinuma et al. |

(Continued)

FOREIGN PATENT DOCUMENTS

| | | |
|---|---|---|
| CN | 204496097 U | 7/2015 |
| JP | 2011-527930 A | 11/2011 |

(Continued)

OTHER PUBLICATIONS

Zeidan, A et al. "Miniature forward-viewing spectrally encoded endoscopic probe", Optics Letters, Aug. 15, 2014, pp. 4871-4874, vol. 39, Issue 16.

Kang, D., et al., "Minature grating for spectrally-encoded endoscopy", Lab Chip, 2013, pp. 1810-1816, vol. 13.

(Continued)

*Primary Examiner* — Abdullah Nur
(74) *Attorney, Agent, or Firm* — Canon U.S.A., Inc., IP Division

(57) ABSTRACT

A novel endoscope, which can be a spectrally encoded endoscope (SEE) probe having forward-view, side-view, or a combination of forward and side views is provided herein. The SEE probe includes a light guiding component, a light focusing component, and a grating component. The probe is configured to forward a light such as a spectrally dispersed light from the grating component to a sample with no intermediate reflections between light guiding component and the grating component. A triangular grating, such as a staircase grating or an overhang grating may be used as the grating component.

26 Claims, 17 Drawing Sheets

(51) Int. Cl.
| | |
|---|---|
| *G02B 5/18* | (2006.01) |
| *G02B 23/24* | (2006.01) |
| *G02B 23/26* | (2006.01) |
| *A61B 1/00* | (2006.01) |
| *A61B 5/00* | (2006.01) |
| *G02B 6/32* | (2006.01) |

(52) U.S. Cl.
CPC .......... *G02B 6/32* (2013.01); *G02B 23/2469* (2013.01); *G02B 23/26* (2013.01)

(56) References Cited

U.S. PATENT DOCUMENTS

| | | |
|---|---|---|
| 4,264,127 A | 4/1981 | Schumacher et al. |
| 5,279,280 A | 1/1994 | Bacich et al. |
| 5,565,983 A | 10/1996 | Barnard |
| 5,909,529 A | 6/1999 | Bhagavatula |
| 6,341,036 B1 | 1/2002 | Tearney et al. |
| 6,377,520 B2 | 4/2002 | Freeman et al. |
| 6,485,413 B1 | 11/2002 | Boppart et al. |
| 6,654,165 B2 | 11/2003 | Engelhardt et al. |
| 6,661,513 B1 | 12/2003 | Granger |
| 6,831,781 B2 | 12/2004 | Tearney et al. |
| 6,858,859 B2 | 12/2005 | Kusunose |
| 7,003,196 B2 | 2/2006 | Ghiron |
| 7,221,454 B2 | 5/2007 | Hampton et al. |
| 7,292,346 B2 | 11/2007 | De Groot et al. |
| 7,330,255 B2 | 2/2008 | Cluzel et al. |
| 7,330,267 B1 | 2/2008 | Weitzel |
| 7,342,659 B2 | 3/2008 | Horn et al. |
| 7,448,995 B2 | 11/2008 | Wiklof et al. |
| 7,796,270 B2 | 9/2010 | Yelin et al. |
| 7,843,572 B2 | 11/2010 | Tearney et al. |
| 7,859,679 B2 | 12/2010 | Bouma et al. |
| 8,045,177 B2 | 10/2011 | Tearney et al. |
| 8,145,018 B2 | 3/2012 | Shishkov et al. |
| 8,203,708 B2 | 6/2012 | Lee et al. |
| 8,289,522 B2 | 10/2012 | Tearney et al. |
| 8,559,014 B2 | 10/2013 | Jeong et al. |
| 8,780,176 B2 | 7/2014 | Yelin |
| 8,804,133 B2 | 8/2014 | Yelin et al. |
| 8,812,087 B2 | 8/2014 | Yelin et al. |
| 8,818,149 B2 | 8/2014 | Shishkov et al. |
| 8,838,213 B2 | 9/2014 | Tearney et al. |
| 9,057,594 B2 | 6/2015 | Kang et al. |
| 9,254,089 B2 | 2/2016 | Tearney et al. |
| 2002/0114566 A1 | 8/2002 | Fairchild et al. |
| 2002/0145815 A1 | 10/2002 | Moriyama et al. |
| 2003/0027328 A1 | 2/2003 | Cunningham et al. |
| 2003/0142934 A1 | 7/2003 | Pan et al. |
| 2004/0147810 A1 | 7/2004 | Mizuno |
| 2004/0174529 A1 | 9/2004 | Maznev et al. |
| 2005/0155704 A1 | 7/2005 | Yokajty et al. |
| 2006/0132766 A1 | 6/2006 | Richman et al. |
| 2007/0188855 A1 | 8/2007 | Shishkov et al. |
| 2007/0233396 A1 | 10/2007 | Tearney et al. |
| 2007/0276187 A1 | 11/2007 | Wiklof et al. |
| 2008/0013960 A1 | 1/2008 | Tearney et al. |
| 2008/0097225 A1 | 4/2008 | Tearney et al. |
| 2009/0141360 A1 | 6/2009 | Koyama |
| 2009/0153932 A1 | 6/2009 | Davis et al. |
| 2010/0210937 A1 | 8/2010 | Tearney et al. |
| 2011/0237892 A1 | 9/2011 | Tearney et al. |
| 2011/0275899 A1 | 11/2011 | Tearney et al. |
| 2012/0112094 A1 | 5/2012 | Kao et al. |
| 2012/0133944 A1 | 5/2012 | Iwasaki |
| 2012/0212595 A1 | 8/2012 | Parmar et al. |
| 2013/0012771 A1 | 1/2013 | Robertson |
| 2013/0331709 A1 | 12/2013 | Le et al. |
| 2014/0221747 A1 | 8/2014 | Tearney et al. |
| 2014/0285878 A1 | 9/2014 | Escuti et al. |
| 2014/0378846 A1 | 12/2014 | Hosoda et al. |
| 2015/0045622 A1 | 2/2015 | Shishkov et al. |
| 2015/0131098 A1 | 5/2015 | Yang et al. |
| 2015/0231841 A1* | 8/2015 | Tearney .......... B29D 11/00663 156/247 |
| 2015/0335248 A1 | 11/2015 | Huang et al. |
| 2016/0341951 A1 | 11/2016 | Tearney et al. |
| 2017/0035281 A1 | 2/2017 | Takeuchi et al. |
| 2017/0168232 A1 | 6/2017 | Tearney et al. |
| 2017/0176736 A1 | 6/2017 | Yamamoto et al. |
| 2018/0084981 A1 | 3/2018 | Wang |
| 2018/0120212 A1 | 5/2018 | Hosoda et al. |

FOREIGN PATENT DOCUMENTS

| | | |
|---|---|---|
| WO | 2014031748 A1 | 2/2014 |
| WO | 2014104405 A1 | 7/2014 |
| WO | 2015093944 A1 | 6/2015 |
| WO | 2015/116951 A2 | 8/2015 |
| WO | 2015116939 A1 | 8/2015 |
| WO | 2015116974 A1 | 8/2015 |
| WO | 2017/024145 A1 | 2/2017 |
| WO | 2017/106347 A1 | 6/2017 |
| WO | 2017/117203 A1 | 7/2017 |
| WO | 2017/139657 A1 | 8/2017 |
| WO | 2017/218496 A1 | 12/2017 |
| WO | 2018/057924 A1 | 3/2018 |
| WO | 2018/132490 A1 | 7/2018 |

OTHER PUBLICATIONS

Kang, D., et al., "Spectrally-encoded color imaging", Optics Express, Aug. 17, 2009, pp. 15239-15247, vol. 17, No. 17.

Moharam, M.G., et al, "Formlation for stable and efficient implementation of the rigorous coupled-wave analysis of binary gratings", J. Opt. Soc. Am. A, May 1995, pp. 1068-1076, vol. 12, No. 5.

Yun, et al., "High-speed spectral-domain optical coherence tomography at 1.3 µm wavelength", Opt Express, Dec. 29, 2003, pp. 3598-3604, No. 11, vol. 26.

Pavillon, N. et al, "Suppression of the zero-order term in off-axis digital holography through nonlinear filtering", Applied Optics, 2009, vol. 48, No. 34, Abstract only.

Harvey KC, et al., "External-cavity diode laser using a grazing-incidence diffraction grating", Opt Letter, Jun. 15, 1991, vol. 16, No. 12, Abstract only.

Yelin, D., et al., "Three-dimensional miniature endoscopy", Nature, Oct. 19, 2006, pp. 765, vol. 443.

Tearney, G.J., et al., "Spectrally encoded miniature endoscopy", Optics Letters, Mar. 15, 2002, pp. 412-414, vol. 27, No. 6.

Pitris, C., "A GRISM-based probe for spectrally encoded confocal microscopy", Optics Express, Jan. 27, 2003, pp. 120-124, vol. 11, No. 2.

Bai, B., et al. "Optimization of nonbinary slanted surface-relief gratings as high-efficiency broadband couplers for light guides", Applied Optics, Oct. 1, 2010, pp. 5454-5464, vol. 49, No. 28.

Barlev, O., et al., "Design and experimental investigation of highly efficient resonance-domain diffraction gratings in the visible spectral region", Applied Optics, Dec. 1, 2012, pp. 8074-8080, vol. 51, No. 34.

* cited by examiner

-1st order diffraction; grating pitch 1 μm

+1st order diffraction

Grating pitch 2.5 µm; red wavelength in center of FOV

+1st Diffraction Order FOV
With reversed wavelength polarity $\lambda = 0.800\ \mu m$ $\lambda = 0.618\ \mu m$ $\lambda = 0.415\ \mu m$ +2nd Diffraction Order FOV
With reversed wavelength polarity $\lambda = 0.800\ \mu m$ $\lambda = 0.618\ \mu m$ $\lambda = 0.415\ \mu m$ +5th Diffraction Order FOV
With reversed wavelength polarity $\lambda = 0.800\ \mu m$ $\lambda = 0.618\ \mu m$ $\lambda = 0.415\ \mu m$

DIFFRACTION ORDERS AND SIGN CONVENTION

Sign Convention: Incident Light and diffraction Light rotate with respect to grating surface "normal": diffraction light rotated clockwise to normal is "negative"; counter clockwise is "positive"

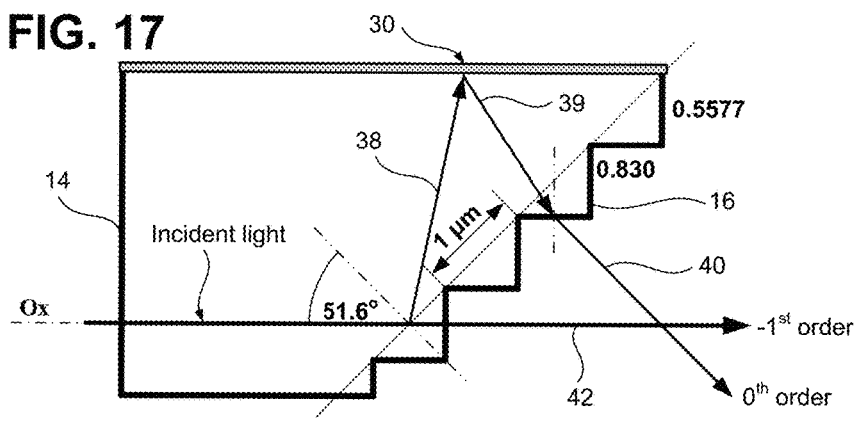
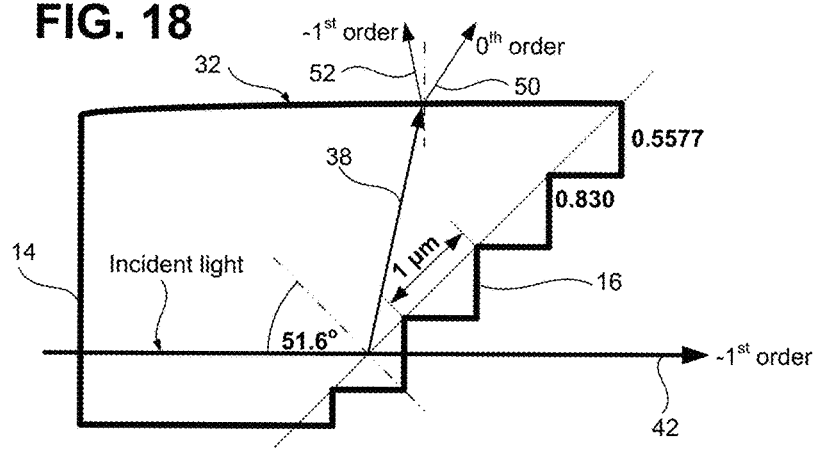
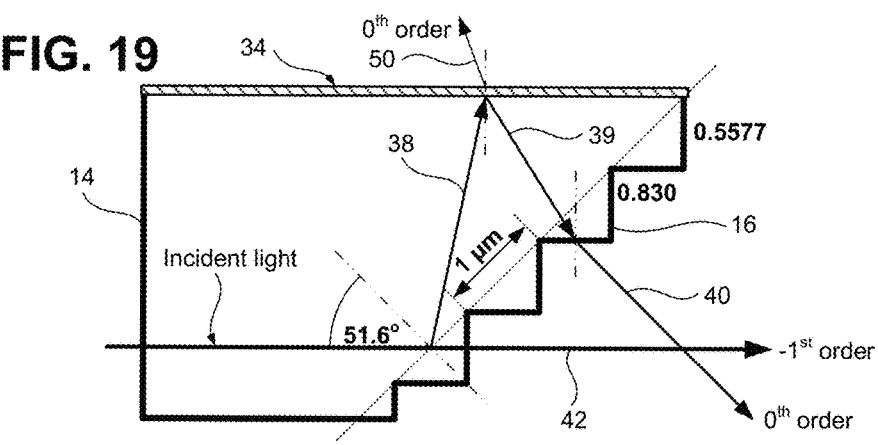

SPECTRALLY ENCODED PROBES

CROSS-REFERENCE TO RELATED APPLICATIONS

This application claims priority from Provisional Application No. 62/363,089 filed Jul. 15, 2016, the disclosure of which is hereby incorporated by reference herein in its entirety.

FIELD OF THE DISCLOSURE

The present disclosure relates to endoscopes. More particularly, the disclosure exemplifies spectrally encoded endoscopic probes.

BACKGROUND INFORMATION

Medical endoscopic probes have the ability to provide images from inside the patient's body. Considering the potential damage to a human body caused by the insertion of a foreign object, it is preferable for the probe to be as small as possible. Additionally, the ability to image within small conduits such as small vessels, small ducts, small needles, cracks, etc., requires a small probe size.

One useful medical probe employs spectrally encoded endoscopy ("SEE"), which is a miniature endoscopy technology that can conduct high-definition imaging through a sub-mm diameter probe. In a SEE probe, broadband light is diffracted by a grating at the tip of an optical fiber, producing a dispersed spectrum of the different wavelengths (colors) on the sample. Light returned from the sample is detected using a spectrometer; and each resolvable wavelength corresponds to reflectance from a different point on the sample. Thus, a SEE probe encodes light reflected from a given point in the sample by wavelength. The principle of the SEE technique and a SEE probe with a diameter of 0.5 mm, i.e., 500 μm have been described by D. Yelin et al., in a publication entitled "Three-dimensional miniature endoscopy", Nature Vol. 443, 765-765 (2006). Another similar example is described by G. Tearney et al., in "Spectrally encoded miniature endoscopy", Opt. Lett., 27(6): p. 412-414, 2002. Imaging with SEE can produce high-quality images in two- and three-dimensions.

Spectrally-encoded endoscopy utilizes the ability of the diffraction grating that deflects incident light to a diffraction angle according to wavelength. When the deflected light hits an object, light is scattered by the object. Detecting the scattered light intensity at each wavelength is equivalent to detecting the intensity from the corresponding diffraction angle. Thus, one-dimensional line image of the object is obtained. A two-dimensional image is obtained by rotating the SEE probe. A three-dimensional image can be obtained by rotating and translating (moving linearly) the SEE probe. Moreover, when incorporated into a sample arm of an interferometer, the SEE probe can also acquire depth information from a sample (e.g., tissue). Typically, as the grating deflects the light, the incident light is usually bent with respect to the optical axis of the probe. In this way, no light goes straight with respect to the optical axis. As no light goes straight, it is not possible with conventional spectrally-encoded endoscopy configuration to view in a forward direction.

Current trend of the spectrally-encoded endoscopy employs side-view type, with a few examples exhibiting forward viewing characteristics. The front-view type consists of multiple components including lenses, spacer elements, prisms and gratings, which makes the probe design complicated. Examples of such designs can be found, for example, in C. Pitris et al., Optical Express Vol. 11 120-124 (2003) and U.S. Pat. No. 8,145,018, both of which disclose a dual prism configuration where a grating is sandwiched between two prisms (a "grism"). This grism directs spectrally dispersed light in the directions including the optical axis of the fiber. The grism consists of multiple components (grating, prisms) which need proper alignment. The need of a grism to construct a forward-view probe increases the cost, complexity of fabrication and size of the probe. Publication WO2015/116951 discloses another forward view endoscope where the angled reflective side surface makes the light incidence angle on the grating such that at least one of the wavelengths propagates parallel to the optical axis of the lens. However, these known designs of forward view SEE probes have drawbacks. First, this design may not allow for use of the full available aperture. A smaller aperture means a decreased achievable resolution.

Second, both designs need a reflective surface in the spacer. This is not particularly easy to fabricate considering the miniature size of the spacer. In particular, the alignment of the spacer and the GRIN lens poses challenges during fabrication.

Further, the illumination fiber is off-axis to the GRIN lens, which introduces additional difficulties in fabrication as well as optical aberrations. In some designs, a reflective coating is needed at least for the second reflective surface, which will introduce light loss and scattering in the system. This coating is also needed for the first reflective surface unless a lower refractive index epoxy is used. A lower reflective index epoxy usually requires special curing conditions, which poses additional concerns for mass production.

Accordingly, it can be beneficial to address and/or overcome at least some of the deficiencies indicated herein above, and thus to provide a new SEE probe having forward direction view and/or omnidirectional view, and an apparatus to use such a probe, e.g., for imaging in a small optics. It is also beneficial to provide a SEE probe having a lower cost and/or less complexity compared to prior known probes.

SUMMARY OF EXEMPLARY EMBODIMENTS

According to at least one embodiment of the invention, there is provided an apparatus comprising a spectrally encoded endoscopy probe comprising: a light guiding component; a light focusing component; and a grating component (e.g., a triangular grating) wherein the probe is configured for guiding a light from the light guiding component, through the light focusing component and to the grating component in the direction of the probe optical axis, and then forwarding a spectrally dispersed light from the grating component towards a sample with no intermediate reflections.

According to at least one embodiment of the invention, there is provided an apparatus comprising a probe that comprises: a light guiding component; a light focusing component; and a triangular grating component, wherein the probe is configured for guiding a light from the light guiding component, through the light focusing component and to the grating component in the direction of the probe optical axis, and then forwarding a diffracted light from the grating component towards a sample with no intermediate reflections.

According to yet other embodiments, there is provided a system comprising a light guiding component; a light focusing component; a grating component, a rotary element, one or more detection fibers, one or more detectors, and one or more processors configured to processes light from multiple diffracted orders and for a single color image based on that light. The probe may be configured for guiding a light from the light guiding component, through the light focusing component and to the grating component in the direction of the probe optical axis, and then forwarding a spectrally dispersed light from the grating component towards a sample with no intermediate reflections.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIG. 17 illustrates an exemplary staircase grating design suitable for an embodiment of the SEE probe having an extended FOV in the forward direction by using a diffracted −1st order and a reflected 0th order.

FIG. 18 illustrates an exemplary staircase grating design suitable for an embodiment of the SEE probe having an extended FOV in the forward direction by using a refracted −1st order and a reflected 0th order and another grating on the side surface.

FIG. 19 illustrates an exemplary staircase grating design suitable for an embodiment of a SEE probe having omnidirectional viewing characteristics using a refracted −1st order and a 0th order reflection and transmission with a second grating surface on a side of the staircase grating.

FIG. 22A is a schematic of the grating design optimized for low reflectance and high transmitted diffraction. FIG. 22B is a schematic of the grating design of FIG. 22A where the details of the beams are magnified.

DETAILED DESCRIPTION OF EMBODIMENTS

Figure 1:
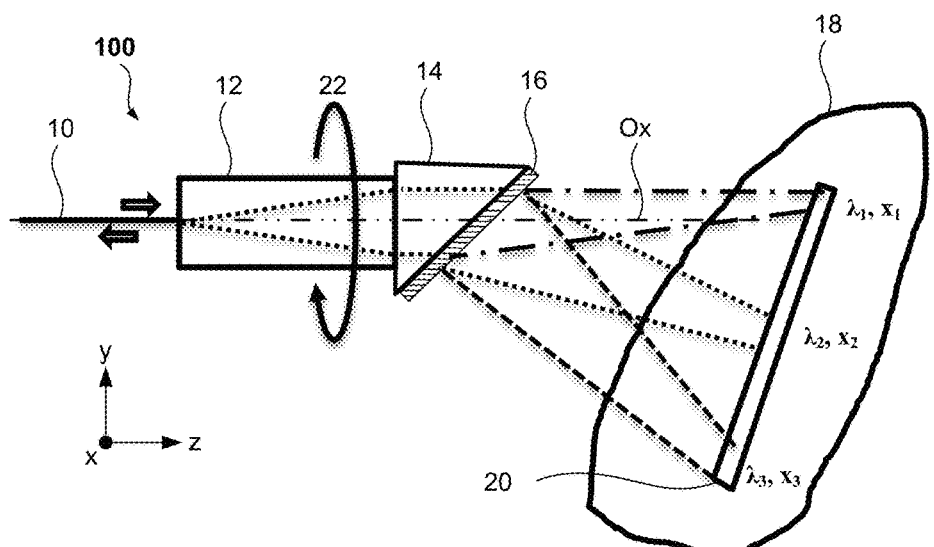
FIG. 1 is a diagram of an exemplary SEE probe according to an exemplary embodiment of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

The embodiments disclosed herein describe SEE probes that can have good resolution in both the scanning direction and the spectral direction due to a fuller use of the diameter available. These embodiments also provide SEE probes without the need for one or more off-axis element in the design and also without the need for a mirror reflection element. The lack of off-axis elements and mirror reflections simplifies the manufacturing process and improves reliability of the probe. Further, due to the use of more limited accepting angles in the collection of reflected light, some embodiments of the SEE probes as provided herein can be designed such that the 0th order and −2nd order will not cause stray light in the system. This is especially true for many designs with substantially no transmitted 0th order light and the reflected 0th order light being at a very large angle.

A diagram of an exemplary embodiment of a SEE probe 100 according to the present disclosure is shown in FIG. 1. This exemplary SEE probe 100 includes an optical fiber 10 (light guiding component), a focusing lens 12 (light focusing component), a spacer 14, and a diffraction grating 16 (grating component). Broadband light (or other electro-magnetic radiation) can be coupled or otherwise provided into the fiber 10, and focused by the lens 12. The light (or other electro-magnetic radiation) travels through the focusing lens 12, the spacer 14, and is incident on the grating 16 without any reflections therebetween. At the grating 16, the light is diffracted according to its wavelength and incident angle. Each light (having a wavelength λ or a wavelength band Δλ) is focused on a unique spatial location on the tissue 18 (sample). As shown in FIG. 1, $X_1$, $X_2$, and $X_3$ are unique spatial locations of tissue 18 for wavelengths $\lambda_1$, $\lambda_2$, and $\lambda_3$, respectively. Therefore, the light (or other electro-magnetic radiation) can be focused into a plane or line 20, rather than onto a point. The plane or line 20 shown in FIG. 1 is referred to as a spectrally-encoded line. One of the wavelengths in the light can propagate substantially parallel to the optical axis (Ox) of the lens 12, shown as $\lambda_1$ in FIG. 1. Light (or other electro-magnetic radiation) reflected by the tissue 18 can be coupled or otherwise provided back to the fiber 10 or to a different fiber (not shown), and then the collected light can be delivered to a detector (not shown) that includes a spectrometer (not shown). At the spectrometer, the spectrum of the returning light (or other electro-magnetic radiation) can be read out as an electrical signal, which can then be used to generate a line image of the tissue using a computer or other digital processor (not shown). The exemplary SEE probe 100 can be scanned rotationally along the optical axis Ox of the lens as shown by the rotational arrow 22, e.g., by rotating or oscillating the lens 12 or in other ways which should be understood to those having ordinary skill in the art.

As shown in FIG. 1 and in other embodiments, no off-axis element is required to provide the forward-viewing design. There is no need for an off-axis element either between the light guiding component and the light focusing component or in any reflections/mirrors prior to the light hitting the grating. This can simplify the manufacturing process and/or improve reliability because alignment of the optics becomes easier compared to previously known SEE probes.

Figure 2:
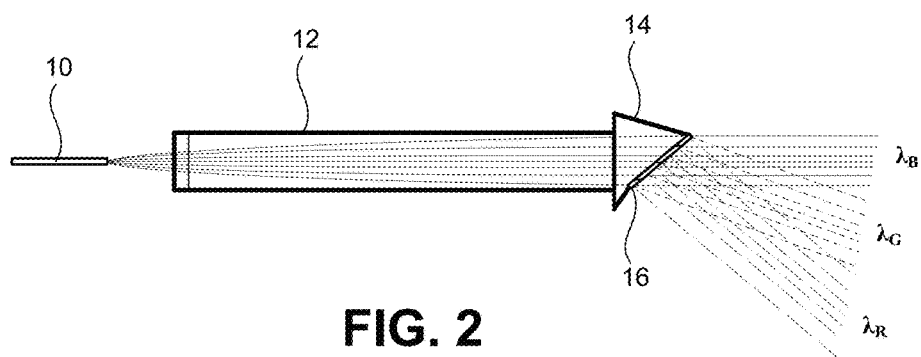
FIG. 2 illustrates spectral dispersion in an embodiment of a SEE probe having forward-view characteristics.

FIG. 2 shows ray tracing of illumination and diffracted light according to one exemplary embodiment. In FIG. 2, the illumination fiber 10 is coaxial with focusing lens 12. The lens 12 is shown in FIG. 2 as a GRIN (graded index) lens for easy fabrication, but a ball lens or other shape of lens may also be used. This embodiment of FIG. 2 specifically optimizes the grating 16 so that the incident angle on the grating will be designed such that at one specific wavelength (e.g. blue, 415 nm), one of its diffraction orders (−1 order in this case) will propagate parallel to the optical axis like it is undiffracted (the diffraction angle is the same as the incident angle).

Figure 3A:
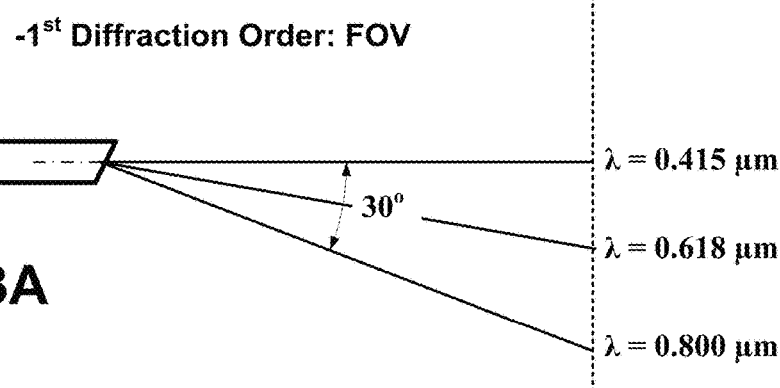
FIGS. 3A, 3B, and 3C illustrate exemplary ray tracing diagrams for the probe shown in FIG. 2.
Figure 3B:
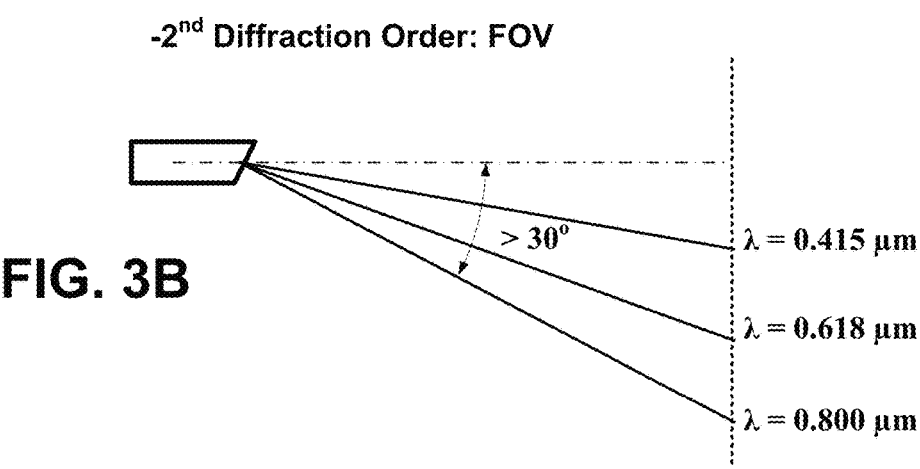

As shown in FIG. 2, after the focusing lens 12, light passes through spacer 14 and then is incident upon the grating 16 with no reflection therebetween. The −1st diffraction order is shown in FIG. 3A. The 0th order will be reflected and is not shown. FIG. 3B shows the −2nd diffraction order for the probe design shown in FIG. 2. Due to limited accepting angles of the detection fiber (e.g. NA=0.5), the 0th order (reflected) and the −2nd order diffracted at a larger angle usually will not cause stray light in the system. The field of view (FOV) can be extended by either increasing the wavelength range or by introducing higher diffraction orders. The FOV can also be extended by increasing the incident angle on the grating as explained later. Table 1 provides light propagation for the various orders at three different wavelengths with an incident angle θi=56.1°.

TABLE 1

| λ | −1st order | −2nd order | −1st order |
|---|---|---|---|
| 0.415 μm | 0° | 33° | 0° |
| 0.8 μm | 30° | 75° | 30° |
| 1.0 μm | — | — | 43° |
| FOV (half angle) | 30° | N/A | 43° |

For the design shown in FIG. 2, the grating period is fixed at about 1 μm for convenience and a blue light (415 nm) was designed to be at the center of the FOV and the red light (800 nm) was designed to be at the edge of the FOV. FIG. 3A shows an exemplary half-angle FOV that can be obtained with the probe design of FIG. 2 using the −1st diffraction order. In other embodiments, other light bands may be used, and other wavelengths or relative wavelengths can be defined as the center and the end of the FOV. Moreover, depending on the desired application, the grating can be designed so that diffractive others are tailored to occupy specific FOV angles. FIG. 3B shows an exemplary half-angle FOV formed by the −2nd diffraction order for the probe design shown in FIG. 2.

In this manner, in the embodiment of FIG. 2, due to limited accepting angles of the detection fiber (not shown), the 0th order and the −2nd order should not cause substantive stray light in the system.

Figure 3C:
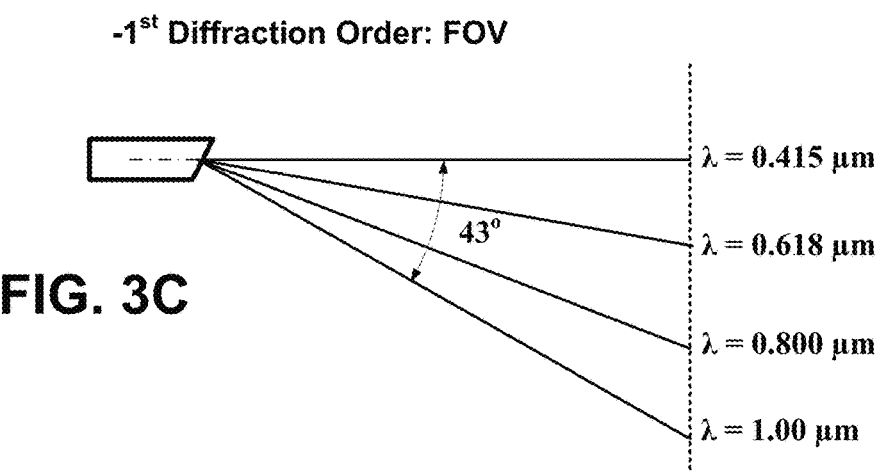

The FOV can be extended by either increasing the wavelength range of the light or by using higher diffractive orders. For example, as shown in FIG. 3C, if the wavelength range is extended from 0.8 μm to 1 μm, the field of view (half angle) is increased from 30° to 43°, as compared to FIG. 3A. One potential issue here is the −2nd diffraction order of the blue light shown in FIG. 3B, which will interfere with the blue portion of the −1st diffraction order (e.g., 415 nm will be covering both center FOV and the FOV corresponds to 830 nm). At least two measures can be taken to address this issue. One is to design the grating to minimize the higher order diffraction efficiencies. The other one is to introduce one more detection fiber to specifically receive higher angle light, e.g. from 30 degrees to 43 degrees. For example, a filter can be introduced or the grating on the detection fiber can be designed such that the blue end wavelength will be filtered out.

In some embodiments, the focusing lens 12 can be a ball lens. The spacer 14 may be formed of a transparent material that supports the grating 16. In other words, spacer material can be a support for grating 16, for example, epoxy material used to align and fix the lens 12 to the grating 16 or a glass material may be used. Alternatively, spacer 14 may be just free space (air) between the lens 12 and grating 16. In practice, spacer 14 may be a transparent wafer substrate on which a plurality of grooves are disposed to form the grating 16.

Figure 4:
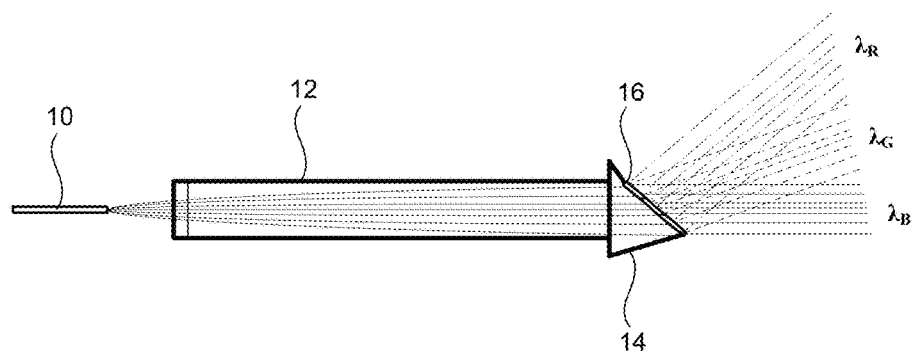
FIG. 4 illustrates an embodiment of a forward view SEE probe having a negative incident angle and the +1st diffraction order.

FIG. 4 shows a probe having a grating 16 designed to diffract +1$^{st}$ order light. As compared to the embodiment shown in FIG. 2, in FIG. 4, the light incident angle on the grating is changed from positive to negative. The diffraction order is also changed from −1$^{st}$ to +1$^{st}$ in this case. Similar to the case shown with reference to FIG. 2 and FIG. 3A, both the 0th order and higher diffraction orders may not introduce stray light due to limited accepting angle from the detection fiber or lower efficiencies of the grating for higher orders of diffraction, or both. Table 2 provides light propagation angles for the first and second positive (+) diffractive orders at three different wavelengths.

TABLE 2

| λ | +1st order | +2nd order |
|---|---|---|
| 0.415 μm | 5° | 30° |
| 0.617 μm | 18° | 57° |
| 0.800 μm | 30° | 84° |

Due to limited accepting angles of the detecting fiber (not shown), the 0th order and the +2nd order will not cause stray light in the system using a probe of this embodiment. As in the previous embodiment, the FOV can be extended by either increasing the wavelength range or by using higher diffraction orders.

For the design shown in FIG. 4, the grating period is fixed at about 1 μm for convenience. For both designs (FIG. 2 and FIG. 4), the blue light (415 nm) will be in the center FOV and the red light (800 nm) will be at the edge of the FOV. However as previously mentioned, other light bands may be used, and other wavelengths or relative wavelengths can be defined as the center and the end of the FOV.

Figure 5:
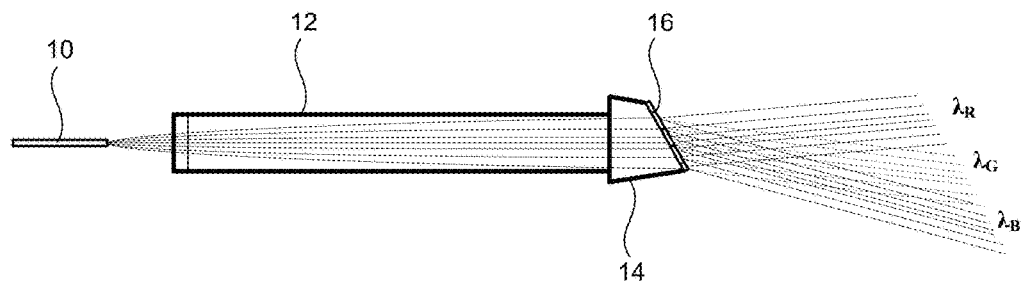
FIG. 5 illustrates an embodiment of a forward view SEE probe having a reversed wavelength polarity design by increasing the grating period.
Figure 6A:
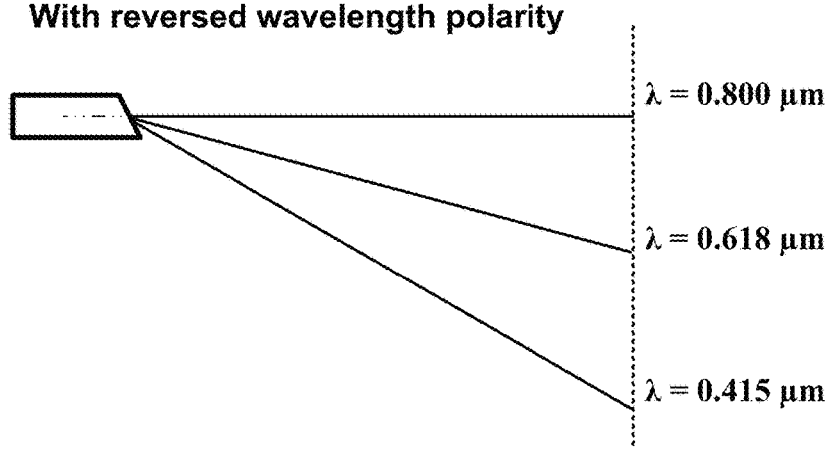
FIGS. 6A, 6B, and 6C illustrate exemplary ray tracing diagrams for the reversed wavelength polarity probe shown in FIG. 5.
Figure 6B:
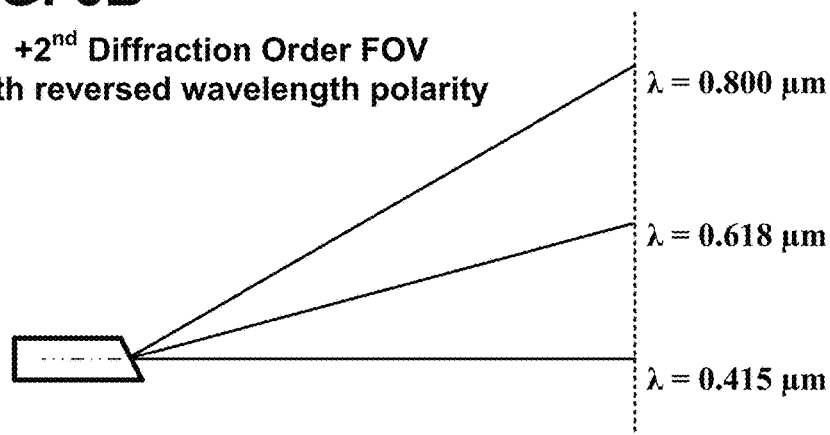
Figure 6C:
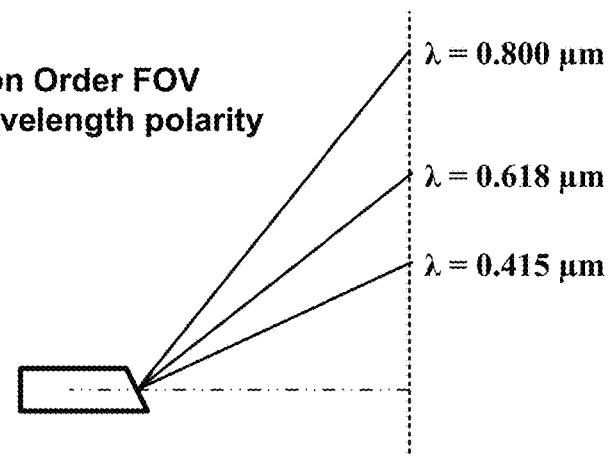

FIG. 5 shows an exemplary embodiment where the pitch of the grating is designed to define specific wavelengths as the center and the end of the FOV. As shown in FIG. 5, the center FOV is now covered by the red (800 nm) light instead of the blue light (415 nm). In this embodiment, the grating period was significantly increased, e.g. from about 1 μm to 2.5 μm. The design changed the wavelength polarity in the FOV. That is, as shown in FIG. 5 the red light is in the center and the blue light is at the edge of the FOV. This can be of particular interest for several reasons. One is that the grating as well as the quantum efficiency of the detector usually has a higher efficiency in the red region. Since the center FOV is usually more important, there would be improved efficiency and/or resolution in this region. This reversed wavelength polarity design may also be particularly useful in a color SEE probe when using the second positive (+2) diffraction order because the +2nd diffraction order will have the blue wavelength in the center and the red wavelength at the periphery of the FOV. Moreover, for this long grating period design, several higher diffraction orders can coexist in the field of view as shown in FIG. 6A-6C. FIG. 6A shows the field of view of the SEE probe shown in FIG. 5 where the red (800 nm) wavelength is in the center of the FOV and the blue (415 nm) wavelength is as the edge of the FOV when using the +1st diffraction order. FIG. 6B illustrates the location of the various wavelengths in the FOV of the second (+2) diffraction order; and FIG. 6C illustrates the location of the various wavelengths in the FOV of the fifth (+5) diffraction order. This phenomena is explained more in detail herein below.

For the long grating period design, several higher diffraction orders can coexist as illustrated in FIG. 6A-6C and summarized in Table 3 for +1st, +2nd, +3rd, +4th, and +5th diffraction orders. In some embodiments, therefore, a grating is designed to particularly enhance the efficiencies of one or more of these higher diffraction orders.

Table 3 provides light propagation angles for the various orders for the embodiment shown in FIG. 5 at three different wavelengths with an incident angle θi=56.1°.

TABLE 3

| Λ | +1st order | +2nd order | +3rd order | +4th order | +5th order |
|---|---|---|---|---|---|
| 0.415 μm | −12.8° | 0.9° | 12.3° | 22.6° | 32.3° |
| 0.617 μm | −5.7° | 12.0° | 27.1° | 41.4° | 55.7° |
| 0.800 μm | 0.0° | 21.1° | 39.8° | 58.4° | 79.6° |

As the +5th order shown in Table 3 can cover a much larger FOV compared to +1st order shown in FIG. 4, it is possible to design a system by using +5th order for side-view applications with a very coarse grating to begin with. This is particularly advantageous as a coarse grating is easier to fabricate and align than a fine-pitch grating.

An embodiment for color imaging using multiple order diffraction is possible using, for example, the structural design shown in FIG. 2. A probe as shown in FIG. 2 is designed such that the incident angle is 81 degrees and the grating groove density is 0.1983 lines/mm. Light beams having center wavelengths of 415 nm, 498 nm, and 622.5 nm are diffracted in forward view direction in −6th, −5th, and −4th order, respectively. Using this probe, 3 monochromatic images are obtained for blue (415-475 nm, −6th order), green (498-570 nm, −5th order), and red (622.5-712.5 nm, −4th order) channels. The half-angle FOV is 29.3 degrees. By combining the 3 monochromatic images using known image processing algorithms, it is possible to obtain a forward view RGB color image of any region of interest scanned by the probe.

Figure 7:
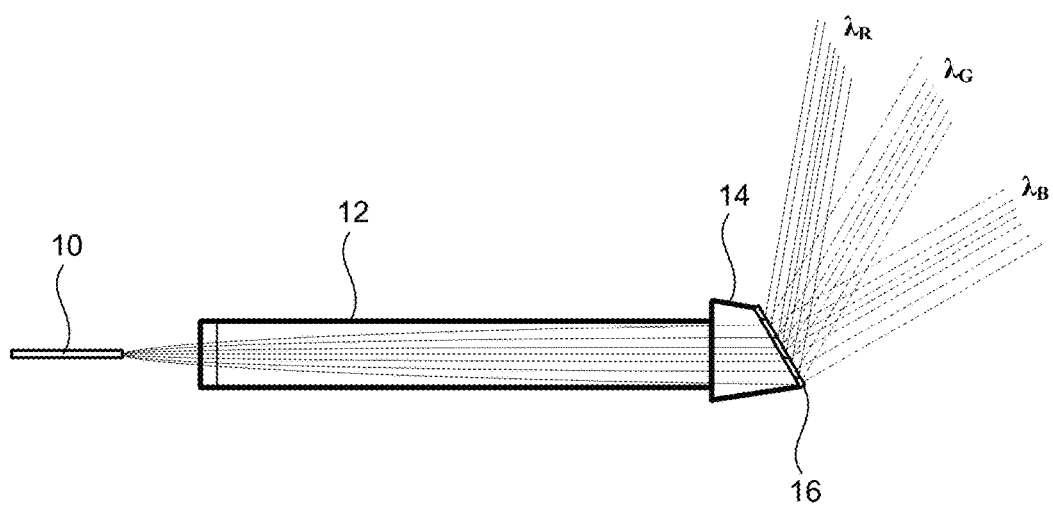
FIG. 7 illustrates an embodiment of a side view SEE probe having an increased FOV based on the +5th order diffracted light of the reversed wavelength polarity.

A side view probe is shown in FIG. 7. This probe is based on the +5th refractive order of the reversed wavelength polarity design shown in FIG. 5. The light incident angle on the grating is 390.8° and the FOV is 47°, (0.415 μm to 0.800 μm). The grating period, however, is 2.5 μm compared to 0.5 μm for other previously known side view designs.

Diffraction Grating Design

Figure 8A:
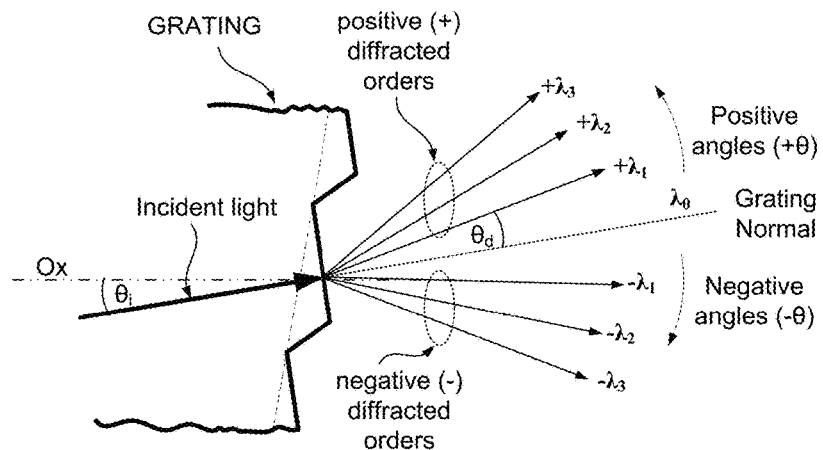
FIGS. 8A and 8B illustrate sign conventions used to derive grating equations described in the various embodiments.
Figure 8B:
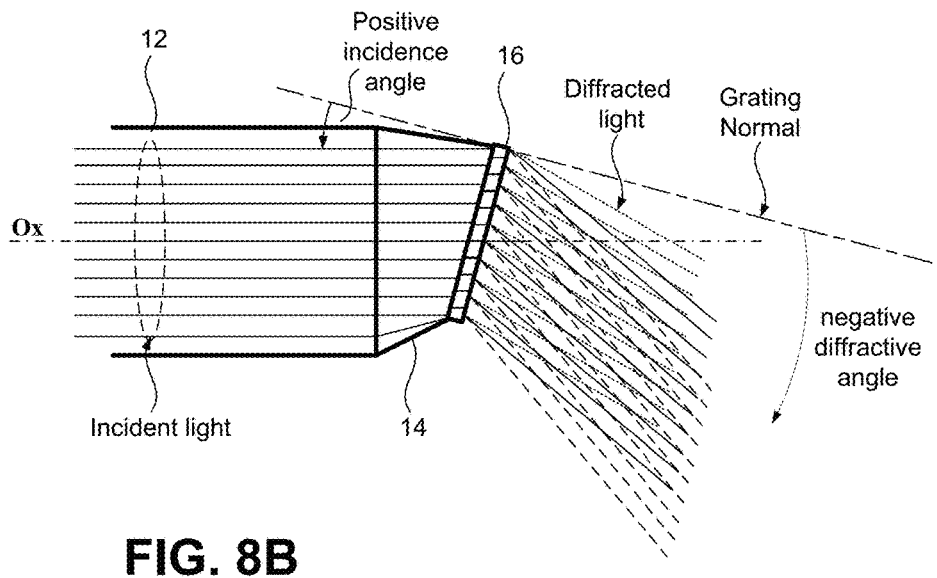

For clarity in the discussion of diffraction orders, the sign convention for the grating equation is provided and shown in FIGS. 8A and 8B. For the incident and the diffracted light, the light is rotated with respect to the grating surface normal. If the rotation of the diffracted light with respect to the normal is clockwise, the sign of the diffracted light is negative (negative angles), as illustrated in FIG. 8B. For the diffraction orders, the diffracted light is rotated with respect to the 0th order light and if the rotation of the diffracted light is counterclockwise with respect to the 0th order, the sign is positive (positive diffracted orders), as show in FIG. 8A.

According to the sign conventions defined in FIGS. 8A and 8B, the grating equation will take the form shown in the following Equation 1, $$-n_i \sin \theta_i + n_d \sin \theta_d = mG\lambda \quad (1)$$

where m is the diffraction order (m=0, ±1, ±2, . . . ), G is the grating spatial frequency (unit: 1/μm), λ is the wavelength of the light in vacuum (unit: μm), $n_i$ and $n_d$ are refractive indexes of the incident light and the diffracted light respectively, and $-\theta_i$ and $\theta_d$ are the incident angle and the diffracted angle as defined by the sign convention shown in FIGS. 8A and 8B.

For the forward view (front-view) design as described herein it means that at least one specific wavelength $\lambda_0$, the incident angle and the diffracted angle satisfy Equation (2).

$$\theta_i = \theta_d \quad (2)$$

Combining Equations 1 & 2, the requirement of the incident light angle can be derived such that Equation (3) is satisfied $$\sin\theta_i = \frac{-mG\lambda_0}{n_i - n_d} \quad (3)$$

The corresponding diffraction angle can thus also be derived from Equation (4):

$$\sin\theta_d = \frac{n_i mG(\lambda - \lambda_0) - n_d m G\lambda}{(n_i - n_d)n_d} \quad (4)$$

Then, the half FOV angle for the forward view probe is determined as: $\Delta\theta = \theta_d - \theta_i$.

Figure 9:
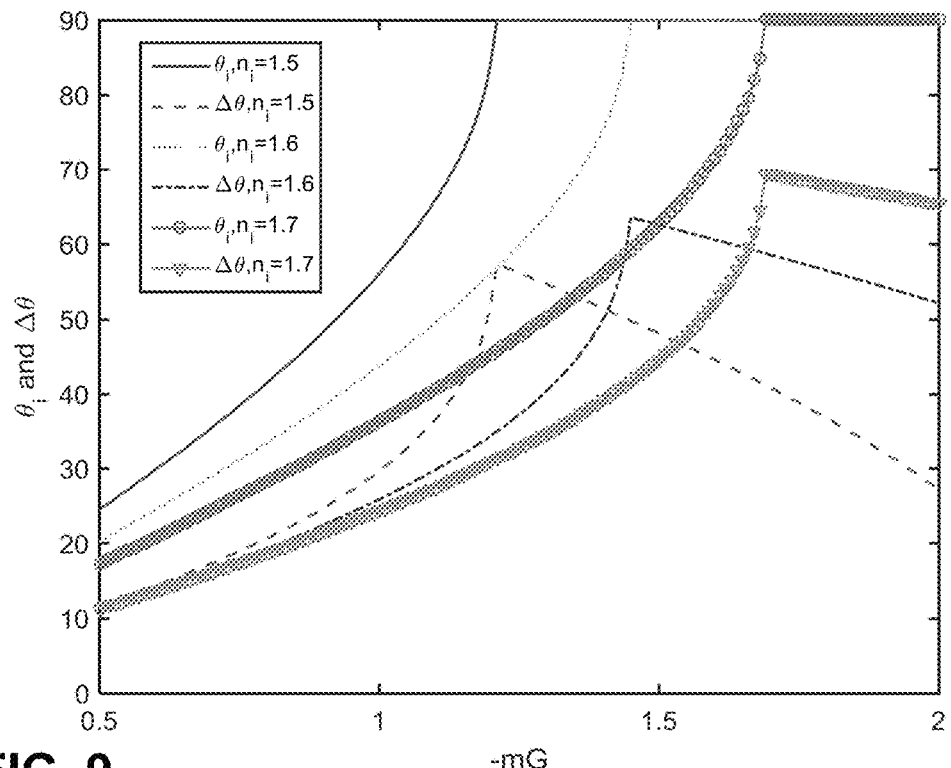
FIG. 9 is a chart showing one embodied solution space for the calculated light incident angle and the half FOV vs. −mG for different refractive indexes of the incident light.

The inventors herein have explored possible light incident angles and their corresponding half FOV angles, as shown in FIG. 9. The calculation is based on Equations 3 and 4, where it is assumed the refractive index of refracted light nd=1 (air), $\lambda 0=0.415$ μm (blue wavelength), and $\lambda=0.8$ μm (red wavelength). According to the plot shown in FIG. 9, it is clear that the half FOV angle will increase as the incident angle on the grating increases. When the incident angle on the grating is getting close to 90°, the resulting half FOV angle will range from 55° (for ni=1.5) to 70° (for ni=1.7) depending on the refractive indexes that the incident light encounters. The design of the grating 16 embodied by FIG. 2 follows the plot shown in FIG. 9.

One solution space for the calculated light incident angle and the half FOV angle vs. -mG for different refractive indexes of the incident light is shown in FIG. 9. The refractive index that the diffracted light observes is assumed to be 1 (i.e., the diffracted light travels through air). These solutions cover the design embodied by FIG. 2.

Figure 10:
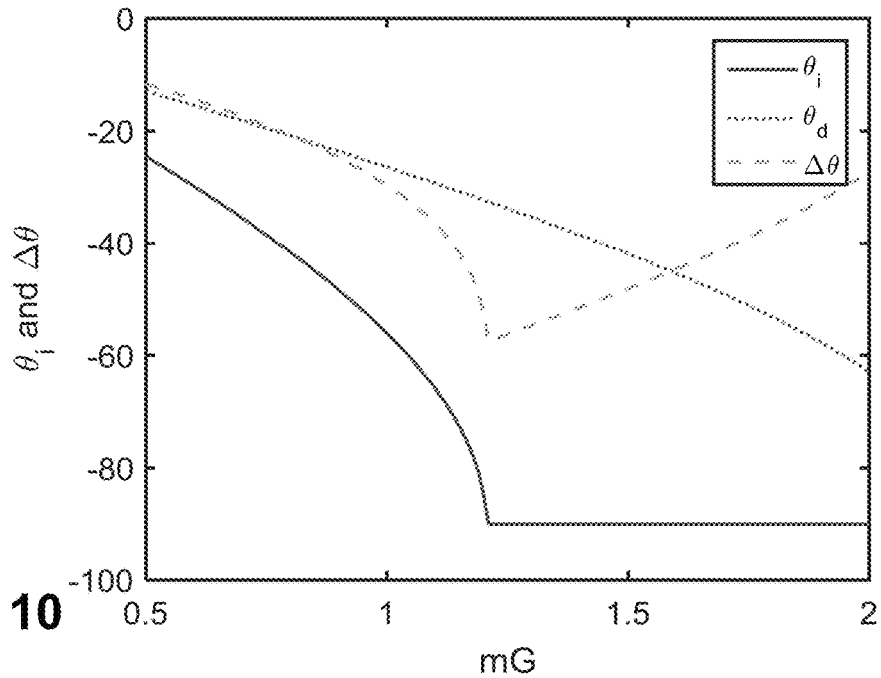
FIG. 10 is a chart showing one embodied solution space for the calculated light incident angle and the half FOV vs. mG for different refractive indexes of the incident light.

Another solution space for the calculated light incident angle and the half FOV angle vs. mG for different refractive indexes of the incident light is shown in FIG. 10. The refractive index that the diffracted light observes is also assumed to be nd=1 and the refractive index that the incident light encounters is assumed to be ni=1.5. The plots of FIG. 10 are numerical solutions corresponding to the design of gratings embodied by FIGS. 4, 5 and 7. This solution space can be understood as the negative sign in Equation (3) is moved to the left side of the equation (i.e. product −1 on both sides of Equation (3)). The incident angle as well as the diffraction order is thus changing the sign.

The reversed polarity solution we observed in the embodiment exemplified by FIGS. 6A-6C can also be explained by Equation (3), i.e. the same light incident angle θi and the same grating constant G corresponds to one or more combinations of mλ0.

In some exemplary embodiments, the incident angle, grating constant (G), and half FOV angle are designed based on the results shown in FIGS. 9 and 10. Due to the symmetry, we only focus on the solutions shown in FIG. 9. If nd=1 (air), ni=1.5 (e.g., corresponding to epoxy OG603 used for our examples), m=−1, $\lambda 0=0.415$ μm, G=1/μm, we have θi=56.1°. The design of the grating shown in FIGS. 4 and 5 is based on these numbers outlined here.

TABLE 4

|  | A | B | C | D |
|---|---|---|---|---|
| incident angle | 60.63° | 65.92° | 71.12° | 81.00° |
| grating constant (G) | 1.05/μm | 1.1/μm | 1.14/μm | 1.19/μm |
| half FOV | 32.78° | 36.62° | 40.64° | 49.03° |

As shown in Table 4, column A, if we increase the incident angle to 60.63°, the grating constant will be G=1.05/μm and the half FOV angle will be 32.78°. If we continue increasing the incident angle to 65.92°, the grating constant will be G=1.1/μm and the half FOV angle will be 36.62° (column B). If the incident angle is 71.12°, the grating constant will be G=1.14/μm and the half FOV angle will be 40.64° (column C). Lastly, when the incident angle is 81.00°, the grating constant for this case will be 1.19/μm and the half FOV angle will be 49.03° (column D).

Grating Formation

Figure 11A:
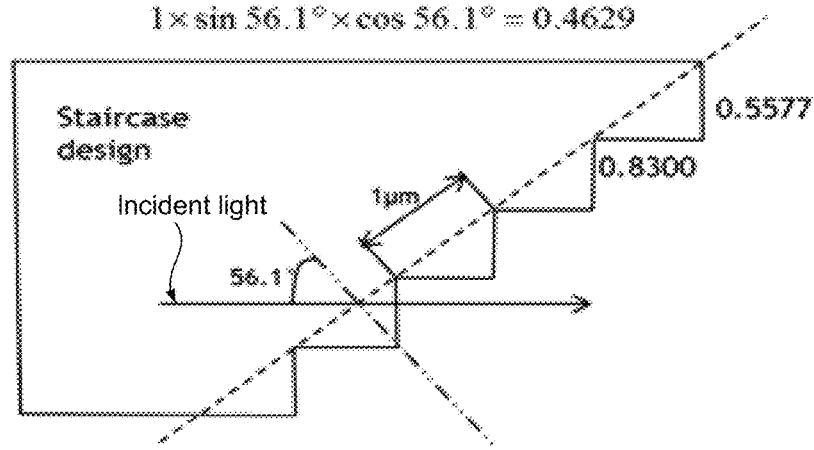
FIGS. 11A and 11B illustrate details of an exemplary staircase grating design for the SEE probe of FIG. 2 where FIG. 11A provides numerical values for the exemplary staircase and FIG. 11B provides the overall grating parameters for fabricating a 20 step staircase grating.
Figure 16:
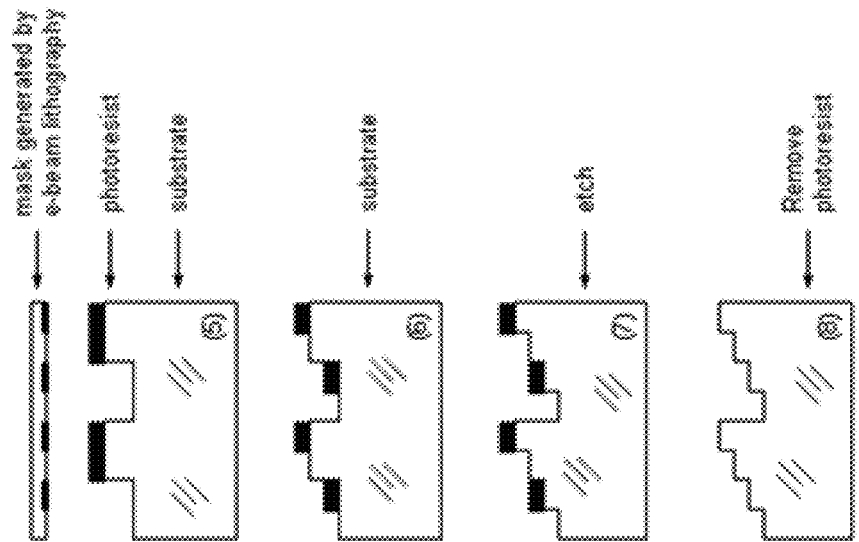
FIG. 16 depicts exemplary grating fabrication method steps for a multi-step binary grating.
Figure 15:
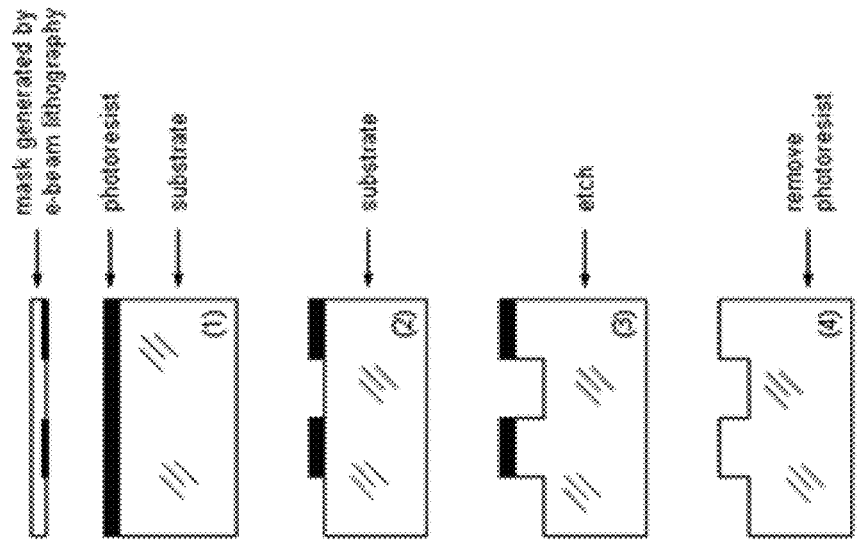
FIG. 15 depicts exemplary grating fabrication method steps for a binary grating.

The gratings used in the probes of the various embodiments of this invention are triangular gratings. Triangular gratings are more generalized blazed grating, whose grating lines possess a triangular, sawtooth shaped cross section. The formed structure can be staircase like as shown in FIG. 11A. FIG. 11A shows a staircase design according to the numerical solution for $\theta_i=56.1°$ and corresponding dimensions thereof of a 1 micron pitch. This staircase design is based on a typical blazed grating, but it is tailored to a specific wavelength to obtain specific results for given parameters $n_d=1$ (air), $n_i=1.5$, m=−1, $\lambda_0=0.415$ μm, and G=μm. Triangular gratings of the type shown in FIG. 11A can be molded with a master which has a complement shape (often times the grating itself) of the desired structure. The fabrication of the master is usually done with photolithography process as shown in FIG. 15 or FIG. 16.

This specific design of the grating shown in FIG. 11A is for the exemplary probe shown in FIG. 2. The staircase design includes embodiments where gratings have a sidewall of the staircase "steps" that are parallel to the optical axis Ox. It also includes staircase designs where the sidewall is not completely parallel, but has an overhang.

Figure 11B:
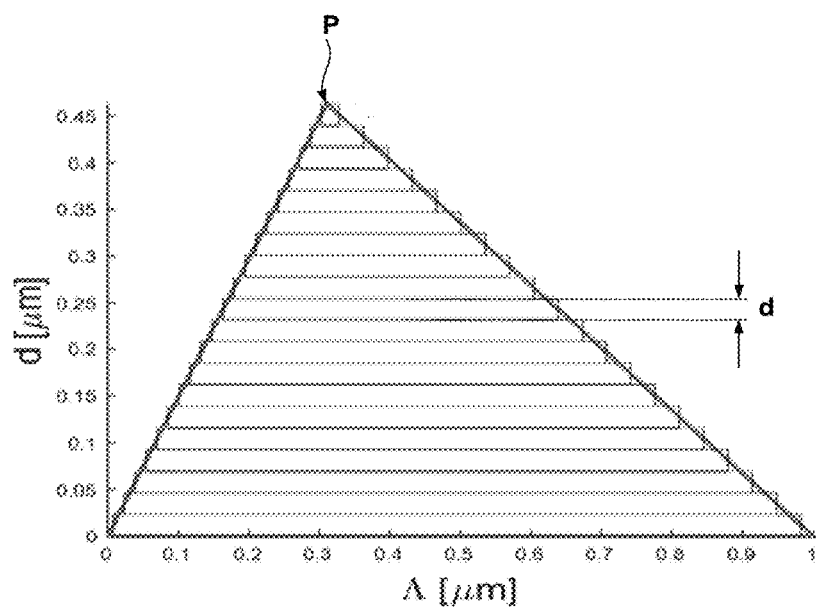

FIG. 11B shows parameters to design a staircase grating, one method is to first optimize the half FOV angle with a reasonable light incident angle according to Equations 3-4. The results of the optimization will be the grating period Λ and the light incident angle θi with a known or expected half FOV angle. Then straight lines, i.e. lines parallel to the optical axis (and thus parallel to the incident light) and perpendicular lines to the parallel lines are drawn to form a staircase profile, hence the name for staircase grating.

The Rigorous coupled-wave analysis (RCWA) has been used to analyze the grating efficiency for the design shown in FIG. 11A. As used herein, grating efficiency refers to the ratio of the diffracted light energy to the incident light energy in a given wavelength (or wavelength region) at a given diffraction order. As understood by those skilled in the art, increasing the number of lines per unit distance (decreasing the pitch) of a grating increases the energy throughput. However, the intention here is design the grating in a manner that the diffraction efficiency is optimized for a specific wavelength at a specific diffraction odder. For the −1st order (negative first order diffraction), the average efficiency is about 30%. In some embodiments, the efficiency is further optimized using different diffraction orders or different pitch, as discussed elsewhere in the various embodiments. TE (transverse electromagnetic) analysis shows a higher diffraction efficiency than TM (transverse magnetic) analysis. As a comparison, the diffraction efficiency for the −2nd order (negative first order diffraction) is much lower for this type of staircase grating design. The diffraction efficiency for the −2nd order can be as low as, for example, less than 0.04 for the entire region and less than 0.02 from 500 to 800 nm. In other embodiments, the grating can be optimized of the −2nd order.

To better understand the energy allocation, the efficiencies were calculated for all the diffraction orders (reflected and transmitted) for both TE and TM modes. In the embodiments disclosed herein, there is no transmitted 0th order. Most of the light at the 0th order is the reflected 0th order for this case. Advantageously, the reflected 0th order light can then be reused for designing a probe with an enlarged FOV, as explained more in detail herein below.

Photolithography can be used to fabricate the grating as disclosed herein. The fabrication method falls into a larger catalog of so called "binary optics", where several masks can be designed specifically to form the structure of interest as shown in FIG. 11B. In the RCWA analysis, grating design with 20 steps in the grating structure was simulated (FIG. 11B). Four masks used in the lithography and shown in this process, are able to provide $2^4=16$ steps in the final design, which should be enough for some applications, where other applications would require a different fabrication method. A specific process that generates up to $2^N$ phase levels from N binary transmission masks can be used to create any grating structure.

The staircase grating design can be a starting point for further optimization. That is, the staircase design can be used when fine tuning the position of the point where two shorter edges of the triangle intersect, i.e. point P shown in FIG. 11B. The optimization can start with, for example, the position of the point P in the grating period Λ and then in the grating height d or vice versa. Once it reaches the local minimum in one direction, we can start searching for the local minimum in another direction. This process continues until the solution converges.

A merit function may be used for this optimization process. One possible merit function should include at least two parameters, one is the average diffraction efficiency for the desired diffraction order. The other one is the minimum diffraction required which, for one embodiment, ranges from approximately 0.4 (400 nm) to approximately 0.15 (800 nm). If needed, a penalty (or weighting) function can be also introduced to consider the 0th order or the higher orders diffractions.

In some embodiments, the grating can be a binary grating. FIG. 15 depicts exemplary grating fabrication method steps for a binary grating. FIG. 16 depicts exemplary grating fabrication method steps for a multi-step binary grating. In general, the most common process for the fabrication of diffractive binary optics involves photolithographic methods that are similar to those used for the fabrication of microelectronics. These methods are based on the use of photoresist deposited on a substrate, etching the photoresist with the use of a mask, and the removal of the photoresist to obtain the desired grating structure. As shown in FIGS. 15 and 16, a plural lithographic masks can be used depending on the desired number of etch levels, and therefore, the desired diffraction efficiency. The processing steps include: (1) placing a desired mask over a substrate coated with photoresist; (2) irradiating the mask with electromagnetic energy (transmitting portions of the mask allows light to expose the photoresist, so the photoresist is removed from the substrate); (3) etching the substrate areas without photoresist to a determined depth (binary step). During etching, the areas of the substrate with photoresist remain impervious to the etching process; (4) removing the remaining photo resist. These four initial steps form a basic binary structure as shown in FIG. 15. After the photoresist is removed to form the binary structure of FIG. 15, the process can be continued form additional levels. Therefore, as illustrated in FIG. 16, the process may further include the steps of: (5) coating the binary structure with photoresist; (6) irradiating a new mask with electromagnetic energy (transmitting portions of the mask allows light to expose the photoresist, so the photoresist is removed from the substrate); (7) etching the substrate areas without photoresist to a determined depth (to from a second binary step). During etching, the areas of the substrate with photoresist remain impervious to the etching process; and (8) removing the remaining photo resist. These processes can be repeated until the desired number of levels is etched into the substrate.

Many different methods exist for the fabrication of diffractive microstructures. Apart from the above described lithographic techniques, direct machining, and replication (e.g., the previously described us of a "master") are well known. The choice of fabrication technique is generally driven by a balance of the desired function and cost.

The fabrication of the master is usually done with photolithography as shown in FIG. 15 and/or FIG. 16. However, for the special grating design shown in FIG. 14, due to the undercut the design cannot be fabricated as a typical blazed grating. Anisotropic etching or other etching methods that could result in undercut such as deep RIE (reactive-ion-etching) can used to create the master. It is worth noting that during fabrication the vertices of the triangle will be rounded and the edge of the triangle can deviate Slightly from a perfect straight line. The definition of staircase or triangular grating here should also include the results due to the fabrication limits/errors/defects when the vertices are rounded or the edges are bended.

Other embodiments may employ triangular gratings that are not staircase gratings per se. For example, the grating may be a triangular overhang grating. The optimization of this grating can be performed in a similar manner to that of the staircase grating. A binary grating design can also provide reasonable diffraction efficiencies with optimization. One issue associated with the binary grating is the higher efficiency for higher diffraction orders. Nevertheless, any type of triangular grating that can provide reasonable diffraction efficiencies with the specified grating period and incident angle may be used in the probes as described herein.

Figure 12A:
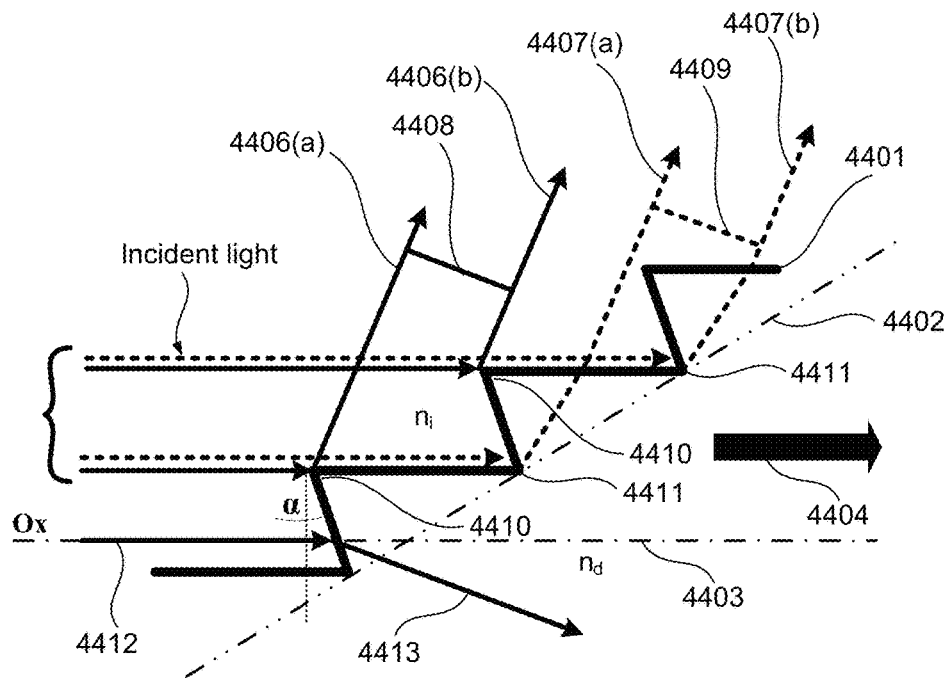
FIG. 12A illustrates a schematic of a staircase grating design optimized for minimized reflectance.
Figure 12B:
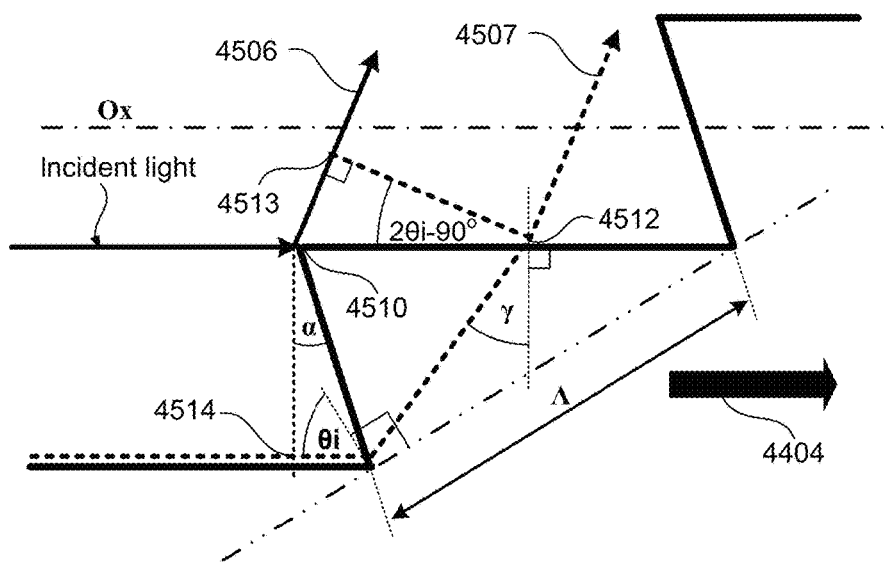
FIG. 12B illustrates a schematic of the grating design of FIG. 12A where the details of the light beams are magnified.
Figure 13A:
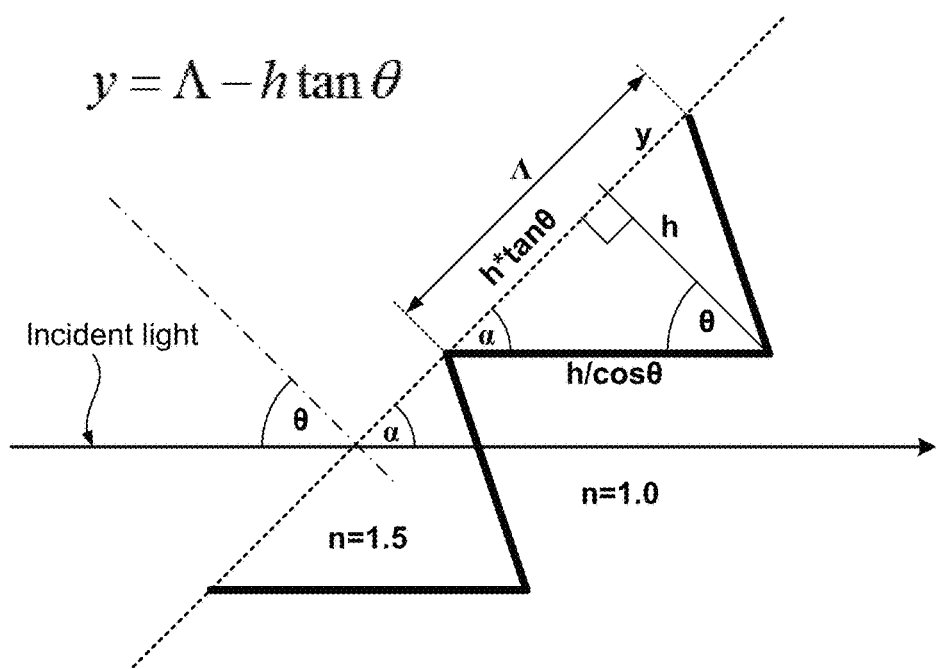
FIGS. 13A and 13B are schematic illustrations of grating optimization.
Figure 13B:
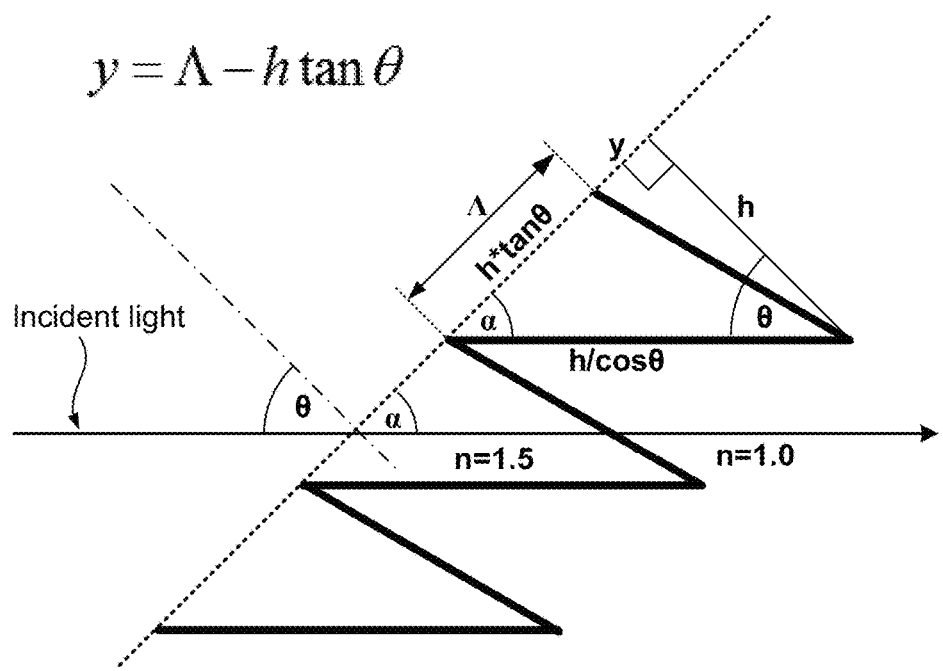

Thus, in some embodiments, the optimization of the grating can be described by FIGS. 12A and 12B as well as FIGS. 13A and 13B. In these figures, probe refractive index, ni=1.5 and the diffracted space medium is presumed to have a refractive index of nd=1.0, and each of the parameters as shown can be optimized. In these optimizations, one edge of the triangle is assumed parallel to the probe axis Ox. The unknown "y" dimension as shown in FIGS. 13A and 13B is thus calculated as the difference between the grating period Λ and product of the grating height h and tangent value of light incident angle θ.

Figure 14:
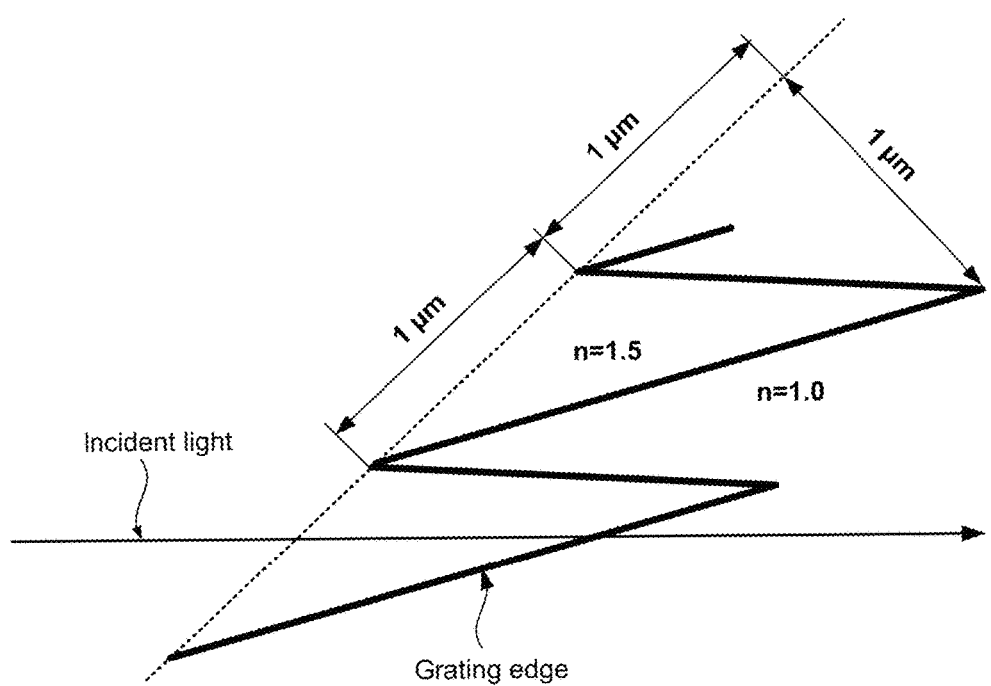
FIG. 14 is a schematic of the grating design optimized for maximum efficiency of diffraction of visible light according to one embodiment.

One optimized grating design that is a triangular overhang is shown is FIG. 14. In this grating, where the refractive indices are defined as nd=1 and ni=1.5, the optimized design provides h=1 and a1=1. This grating provides a minimum efficiency of 65% from 400 nm to 800 nm and has an average efficiency of greater than 75% over the same range.

In some embodiments, the grating fabrication methods as described by B. Bai et al. (Appl. Opt. 2010 Oct. 1, 49(28): 5454-64) may be used. Bai has described the fabrication and replication of the slanted overhanging grating couplers that can be realized using known microfabrication technologies, including EBL, RIE, RIBE, and UV replication.

In some embodiments, the fabrication methods as described by O. Barley et al. (Appl. Opt. 2012 Dec. 1 51(34) 8074-80) may also be used. Barley formed surface-relief resonance-domain diffraction gratings having deep and dense grooves. Barley used a process having the steps of "(a) recording a resonance-domain grating pattern in e-beam resist layer with e-beam lithography, (b) transferring the recorded spatial pattern to a fine metal mask, and (c) transferring the spatial pattern from the metal mask to the substrate of the resonance-domain grating using reactive ion etching (RIE) technology." These and other fabrication methods are believed to be well within the knowledge of those skilled in the art to which the present invention pertains.

Increased FOV

As explained previously, for several embodiments, the 0th order is reflected. Thus, it is useful to reuse/recycle this 0th order light. The 0th order light can be reused to increase the FOV. FIG. 17 illustrates an embodiment of a staircase grating configured to reuse the reflected 0th order light to increase the FOV. The −1st order light 42 exits the grating 16 as forward view light. The reflected 0th order light 38 is further reflected by, for example, a total internal reflection (TIR) sidewall or a reflective coating 30, and the internally reflected 0th order light 39 will re-enter the system at a different angle, and re-interact with the staircase (blazed) grating 16 as a reflection 40. For this design, the reflective surface 30 needs to be optically flat, i.e. fine-polished or injection molded. It is possible to introduce a mild curvature on this surface for injection molded parts to correct aberrations in the optical system, if necessary. As illustrated in FIG. 17, the −1st order light 42 exits the grating 16 parallel to the probe optical axis Ox, and serves as forward view light. On the other hand, the light of reflection 40 (reused 0th order) exits the grating at a negative angle with respect to the optical axis, and thus serves as side view light. Therefore, two detection fibers are preferably used with this embodiment of FIG. 17, i.e. one for forward view and one for the side view light. Due to limited accepting angles, the 0th order and the −2nd order will not cause stray light in the system. On the contrary, when the grating is properly designed with an optimized sidewall 30, the grating can use the 0th order to increase the FOV.

FIG. 18 illustrates another grating having a sidewall surface 32 on the side thereof substantially parallel to the optical axis. Again, the grating sidewall surface 32 can have a mild curvature for aberration corrections. The 0th order reflected light 38 from the first surface of grating 16 will function as the incident light and interact with the sidewall surface 32. The sidewall surface 32 can be formed as a second diffractive grating, which can diffract the 0th order reflected light 38 into diffracted light 50 and diffracted light 52. The diffracted light 50 and 52 from the sidewall surface 32 (second grating) functions as the illumination for side view or even back view purposes, depending on the selected orders such as −1st, −2nd, etc. In FIG. 18, the light diffracted by the sidewall 32 is shown as −1st order light 52 and 0th order light 50. However, the sidewall 32 (second grating) can also be designed to diffract specific desired orders of diffraction at desired angles of illumination. On the other hand, in FIG. 18, the original −1st order light 42 propagated parallel to the optical axis and serves as forward view light. Again, two detection fibers are preferably used for this system, i.e. one for forward view and one for side view (or back view).

A combination of the grating configurations shown in FIGS. 17 and 18 can make possible an omni-directional SEE probe. An example of a grating configured to implement an omni-directional SEE probe is shown in FIG. 19. According to FIG. 19, the reflected 0th order light 38 reflected from the first surface of grating 16 will interact with a sidewall surface 34. The sidewall surface 34 is designed as a second grating such that it will diffract the 0th order light 38 into diffracted light 50 for back view and will also reflect light 39 for side view purposes. The reflected light 39 will interact with the first surface of grating 16 again for side-view illumination. The diffracted light 50 from the sidewall surface 34 (second grating) functions as the illumination light for back view purposes, depending on the diffracted orders such as 0th, −1st, −2nd, etc. Three detection fibers are needed in the case of FIG. 19, i.e. one for forward view, one for side view and one for back view. In this manner, a true omni-directional viewing probe can be provided with a minimum number of optical elements.

Figure 20:
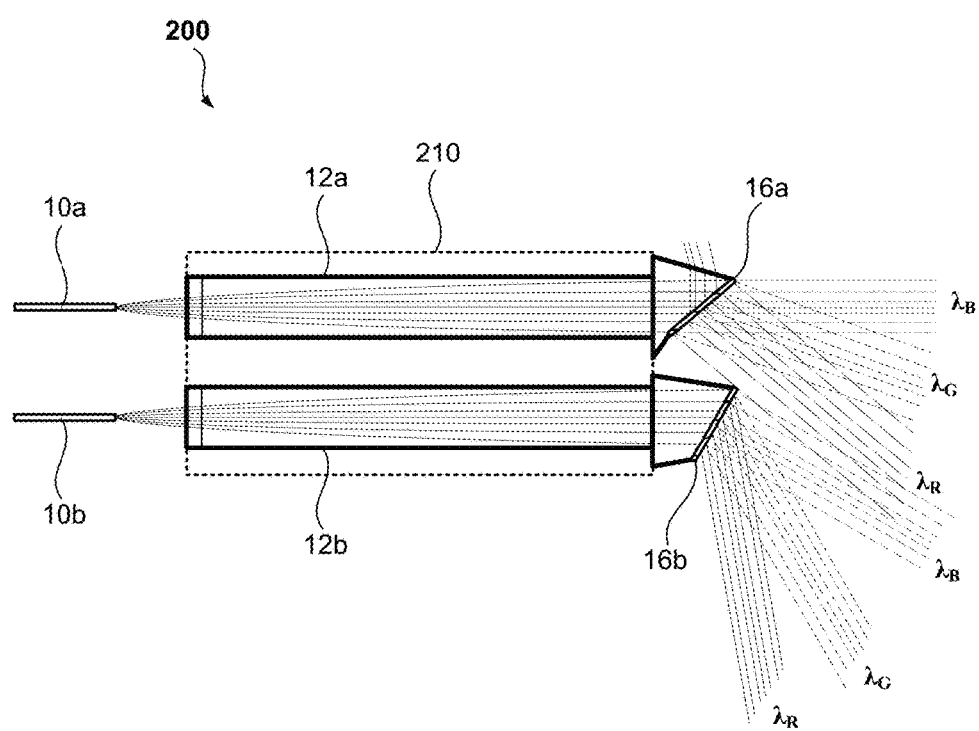
FIG. 20 illustrates an exemplary embodiment of a SEE probe having two illumination fibers and two staircase gratings for an extended FOV.
Figure 21:
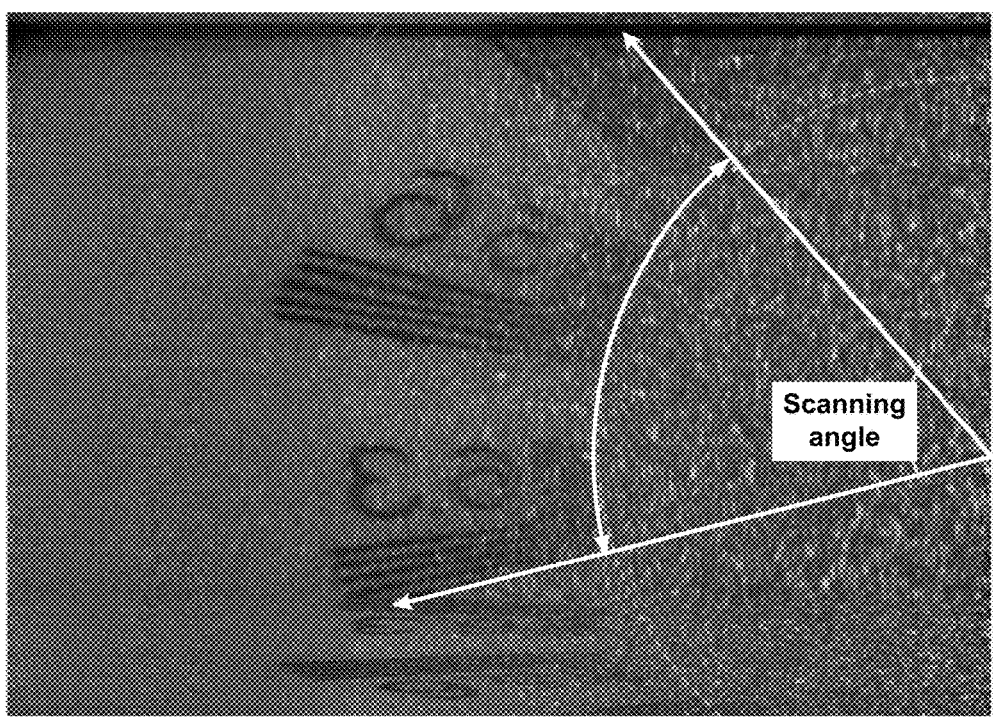
FIG. 21 is an image acquired with a SEE probe designed according to the design shown in FIG. 20.

The designs shown in FIGS. 17-19 provide an enlarged FOV with only one illumination fiber. It is possible to design the grating slightly differently to enlarge the half FOV coverage even further, by introducing one or more additional illumination fibers. One example is shown in FIG. 20, where a see probe 200 includes first and second illumination fibers 10a and 10b, first and second GRIN lenses 12a and 12b, and first and second gratings 16a and 16b arrange within a common sheath 210. According to the SEE probe 200 of FIG. 20, 0° to 30° of the FOV is covered by the forward view design described above in in reference to FIG. 2. And 30° to 80° of the FOV is covered by a side view probe design, as the one described above in reference to FIG. 7 (except with negative diffraction angles). As described above, for the forward view probe, the grating period can be 2.5 μm with an incident angle of 49.6. For the side view probe, the grating period is 0.5 μm with an incident angle of 25.4°. Binary grating is used here for both forward view and side view, which is optimized for highest diffraction efficiency at −1st order.

The inventors herein have simulated the imaging quality obtainable with the forward probe view design shown in FIG. 20. Calculated spot diagrams and the RMS wavefront errors have shown that the imaging quality is close to (but not at) the diffraction limit for the forward view probe. Thus, further optimization according to the methods provided herein will further optimize this grating to reach the diffraction limit. For the simulated side view probe of FIG. 20, diffraction limited imaging can be achieved in the wavelength range centered around 0.63 μm.

A probe following the design of FIG. 20 has been made and tested. The side view probe section has a FOW with void space below 30°; this void space in the FOV is filled by the forward view probe design, as shown in FIG. 20. Tests performed by the inventors resulted in an acquired image being distorted. However, such distortions can be numerically corrected afterwards using known image processing algorithms. Due to the limit of the scanning motors, the inventors have been able to only scan an angle range of about 70°. A full circle can be scanned properly by modifying the motor and introducing a rotary junction. Table 5 summarizes the imaging wavelengths and FOV angles obtained with the configuration of the SEE probe 200 shown in FIG. 20.

TABLE 5

| λ | Forward View FIG. 20 | Side View FIG. 20 |
|---|---|---|
| 0.415 μm | 0° | 30° |
| 0.617 μm | 17° | 61° |
| 0.8 μm | 30° | 82° |

Minimizing Reflection in the Grating

Figure 22A:
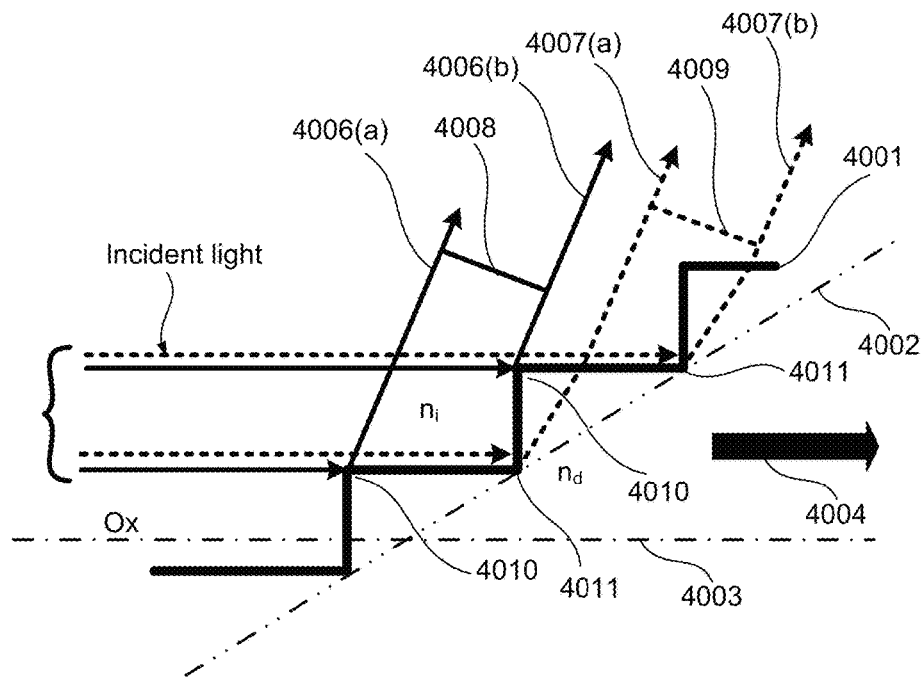
FIGS. 22A and 22B illustrate examples of staircase grating optimization.
Figure 22B:
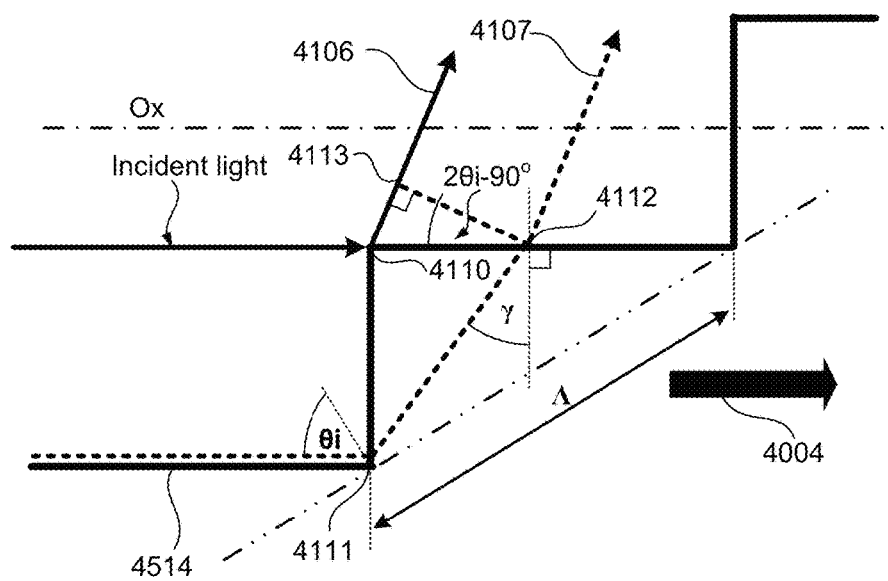

An alternative grating design to the staircase grating design shown in FIG. 11 is explained in reference to FIGS. 22A and 22B. This design is optimized for low reflectance and high transmitted diffraction. FIG. 22A depicts a cutaway on the plane grating along the optical axis and perpendicular to grating plane. For this design, 4002 is the grating plane, and 4001 is the physical edge (shape) of the staircase grating. The optical axis (Ox) of the probe is shown as numeral 4003 and the forward direction light (diffracted light), which is parallel to the optical axis, is shown as arrow 4004. The upper left part of the figure is the probe spacer material of refractive index (ni), where ni=1.5. The lower right part of the figure is assumed to be air or diffracted space medium with refractive index (nd), where nd=1.0. For this design, a wavelength range of 415 to 830 nm or a similar range is contemplated. The grating follows the equations (1) through (4) of the previously presented embodiments and for a specific wavelength λ0=415 nm. Reflected rays 4006(*a*) and 4006(*b*) with wavefront 4008 are the reflection caused by coupling of waves from the scatter at the upper ridges 4010 of the grating. Reflected rays 4007(*a*) and 4007(*b*) with wavefront 4009 are the reflection caused by scatter at the lower ridges 4011 of the grating. The grating shape is optimized such that the reflected wavefronts 4008 and 4009 interfere destructively, so that effects of the reflection will be low. For this optimization, optical path difference of rays 4006(*b*) and 4007(*a*) are calculated as explained below.

In FIG. 22B, it can be seen that as the beams 4107 and 4106 travel from the left, the path difference can be calculated with the paths from the equi-phase points, 4111 and 4110. Path 1 of beam 4107 from point 4111 to point 4112 is $$\text{Path1} = -n_i \Lambda \cos\theta_i \cos 2\theta_i \tan\gamma \quad (5)$$

Path 2 of beam 4106 from point 4110 to point 4113 is:

$$\text{Path 2} = \frac{n_d \Lambda \cos\theta_i}{\cos\gamma} \quad (6)$$

Λ is the pitch of the grating and is the inverse of grating constant G. In order to have destructive interference the path difference between the two rays or wavefronts must have path length equal to integral multiple of the wavelength and a half wavelength. This wavelength can be chosen independent of the forward propagating wavelength λ0=415 nm.

$$\text{Path1} - \text{Path2} = (k+\tfrac{1}{2})\lambda, \ [k=0,\pm1,\pm2,\dots] \quad (7)$$

Angle γ is determined from Snell's law of refraction as:

$$\sin\gamma = -\frac{n_i}{n_d}\cos 2\theta_i \quad (8)$$

Using these equations, one exemplary design is summarized in Table 6. For this embodiment, the shortest wavelength, 415 nm, is chosen for minimizing the reflection, thus maximizing the transmitted diffraction at that wavelength. The path difference is 622.5 nm which is 1.5 times the wavelength of 415 nm. Rigorous coupled wave analysis (RCWA) calculation for the grating of one example provide good efficiency for both TM and TE light. In this example, the efficiency of TE is approximately between 0.6 (400 nm) and 0.3 (800 nm). For TM light, the efficiency ranges approximately between 0.5 to slightly over 0.1.

TABLE 6

| Parameter | Value | Unit |
|---|---|---|
| λ$_o$ | 415 | nm |
| n$_i$ | 1.5 | |
| n$_d$ | 1 | |

TABLE 6-continued

| Parameter | Value | Unit |
|---|---|---|
| Path difference | 622.5 | nm |
| θ$_i$, θ$_d$ | 51.47 | deg |
| Pitch | 1061 | nm |
| γ | 19.63 | deg |

Another exemplary embodiment of grating design for minimized reflection is explained using FIGS. 12A and 12B where the probe and the system can function, as previously described with reference to FIG. 2, in a forward view imaging mode. This design is optimized for low reflectance and high transmitted diffraction similar to FIG. 2, but also is optimized with blazed angle of the grating for higher diffraction efficiency. FIGS. 12A and 12B depicts a cutaway on the plane grating along the optical axis and perpendicular to grating plane. These figures are greatly enlarged to view a portion of the grating structure for ease of explanation. It is noted that the grating is shown as having locally flat surfaces and linearly defined edges, but the various embodiments of this invention may be applied to planer as well as slightly curved (concave or convex) surfaces.

For the design shown in FIG. 12A, 4402 is the grating plane and 4401 is the physical shape (edge) of the step (staircase) grating. The optical axis Ox of the probe is shown as 4403, and the forward direction light, which is parallel to the optical axis, is shown by 4404. The plane of the embodiment shown in FIGS. 12A and 12B is intentionally tilted by the blazed angle α on this grating to form blazed grating so that Snell's law of refraction applies to the beam 4412 to refract and diffract into the direction of beam 4413. The equation for such condition is as follows:

$$\sin\alpha = \frac{n_d}{n_i}\sin(\theta_i - \theta_{dc} + \alpha) \quad (9)$$

which is the same as:

$$\tan\alpha = \frac{n_d \sin(\theta_i - \theta_{dc})}{n_i - n_d \cos(\theta_i - \theta_{dc})} \quad (10)$$

The upper left part of the figure is the probe spacer material of refractive index, n$_i$=1.5. The lower right part of the figure is assumed to be air or diffracted space medium with refractive index, n$_d$=1.0. For this design, wavelength range of 415 to 830 nm is used. The grating follows the equations (1) through (4) of the previously presented embodiments, for a specific diffracted wavelength λ$_o$=415 nm. And the blazed angle can be independently chosen for wavelengths other than λ$_o$.

In FIG. 12A, reflected rays 4406(*a*) and 4406(*b*) with wavefront 4408 are the reflection caused by coupling of waves from the scatter at the upper ridges 4410 of the grating. Reflected rays 4407(*a*) and 4407(*b*) with wavefront 4409 are the reflection caused by scatter at the lower ridges 4411 of the grating. The grating shape is optimized such that the reflected wavefront 4408 and 4409 interfere destructively, so that effects of the reflection will be low. For this optimization, optical path difference of rays 4406(*b*) and 4407(*a*) are calculated as explained below.

As shown in FIG. 12B, as the beams 4507 and 4506 travel from the left, the path difference can be calculated with the paths from equi-phase points 4514 and 4510.

Path 1 of beam 4507 from point 4514 to point 4512 is:

$$\text{Path1} = -n_i \Lambda \cos\theta_i \cos 2\theta_i (\tan\alpha + \tan\gamma) \quad (11)$$

Path 2 of beam 4506 from point 4510 to point 4513 is:

$$\text{Path 2} = \Lambda\cos\theta_i\left(n_i\tan\alpha + \frac{n_d}{\cos\gamma}\right) \quad (12)$$

$\Lambda$ is the pitch of the grating and is the inverse of grating constant G. In order to have destructive interference, the path difference between the two rays or wavefronts must have path length equal to integral multiple of the wavelength and a half wavelength. Again, this wavelength can be chosen independent of the forward propagating wavelength $\lambda_0 = 415$ nm.

$$\text{Path1} - \text{Path2} = (k+\tfrac{1}{2})\Lambda, \ [k=0,\pm 1,\pm 2,\ldots] \quad (13)$$

Angle $\gamma$ is determined from Snell's law of refraction at point 4112, as:

$$\sin\gamma = -\frac{n_i}{n_d}\cos 2\theta_i \quad (14)$$

Due to the configurations of the staircase gratings, grating steps and diffraction rays, only a few conditions exist, which must be satisfied to minimize the effects of reflection in the grating.

Using these equations, one example design is summarized in table 7 shown below. For this embodiment, the center wavelength, $\lambda_c = 622.5$ nm, is chosen for minimizing the reflection, thus maximizing the transmitted diffraction at that wavelength in the forward direction. The path difference is 933.75 nm, which is 1.5 times the wavelength chosen. The center wavelength of $\lambda c = 622.5$ nm is also used for the blaze angle optimization, in order to increase the overall diffraction efficiency over all the wavelengths. Rigorous coupled wave analysis (RCWA) calculation for the grating of this embodiment using the design parameters of Table 7 provides an efficiency of approximately 0.4. The efficiency of a grating having this parameters this embodiment was also acceptable, having a higher TE with Emax=0 56 and a min=0.3 at 800 nm. TM has a similar maximum at blue $\lambda$ and a min of 0.2 (at 800 nm). The overall diffraction efficiency over the full spectrum range for −1st order diffraction is higher than that for the grating described in reference to Table 6.

TABLE 7

| Parameter | Value | Unit |
| --- | --- | --- |
| $\lambda$ | 415 | nm |
| $n_i$ | 1.5 | |
| $n_a$ | 1 | |
| Path difference | 933.74 | nm |
| $\theta_i, \theta_d$ | 52.77 | deg |
| $\lambda_c$ | 622.5 | nm |
| $\theta_{dc}$ | 36.67 | deg |
| Pitch | 1042 | nm |
| $\gamma$ | 23.70 | deg |

In this design, the field of view (FOV) can be extended by using additional orders of light (e.g., the the reflected 0th order. It is even possible to have an omni-directional probe design, as described above.

In this and other embodiments, a grating with a much larger period (e.g. $\Lambda > 1.5$ μm) can be used in combination of higher diffraction orders (m>1) for side view probes with a larger FOV. In our design example, if we use the blazed grating to enhance the $5^{th}$ order diffraction, even with a grating period of 2.5 μm, it is possible to achieve a larger FOV of 47°.

Some embodiments provide a grating with a large overhang, as shown in FIG. 14. One particular advantage in the various embodiments of the invention as described herein is that the probe can have improved resolution compared to prior SEE probes in one or both of the scanning direction and the spectral spectral direction since these embodiments provide the ability to use the full diameter available on the probe.

Another particular advantage in the various embodiments of the invention is that, due to limited accepting angles of the detecting fiber or fibers, the $0^{th}$ order and the $-2^{nd}$ order will not cause significant stray light in the system. This is especially true as for the many embodiments described herein having no transmitted $0^{th}$ order light. In many instances, the reflected $0^{th}$ order light is at a very large angle and will not significantly cause stray light. Advantageously, in some embodiments, the reflected $0^{th}$ order light can be reused (redirected) to increase the FOV angle of the probe. Further advantageously, the steps and blaze angle of the grating can be designed to minimize effects of the $0^{th}$ order reflected light by causing destructive interference of reflected light.

Imaging System

Figure 23:
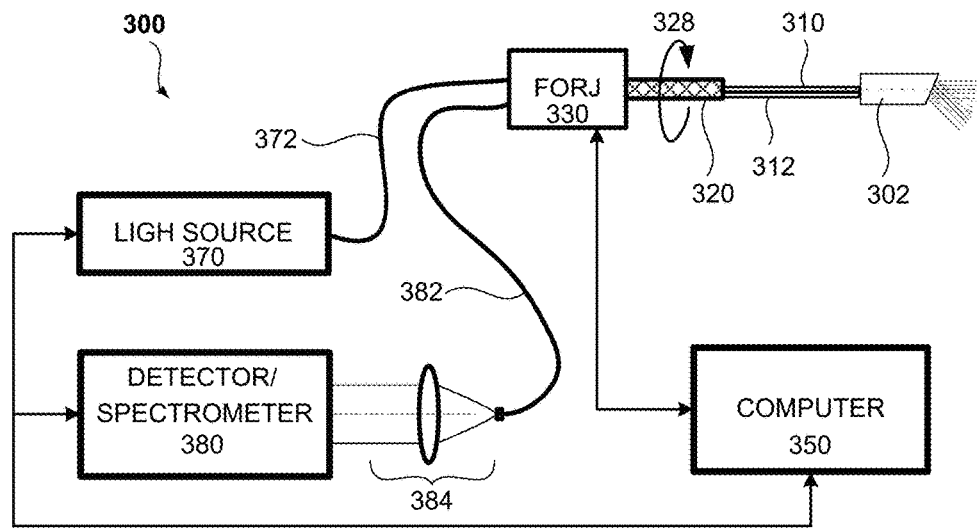
FIG. 23 is a diagram of an imaging system including the SEE apparatus according to an exemplary embodiment of the present disclosure.

A system to acquire an image from the SEE probe according to an exemplary embodiment of the present disclosure is shown in the diagram of FIG. 23. The system 30 of FIG. 23 includes, for example, a light source 370, a detector/spectrometer 380, a fiber optic rotary joint (FORJ) 330, a probe 302, and an image processing computer 350. The light source 370 outputs light of broadband spectrum (or other electro-magnetic radiation). The range of the wavelength can be within the visible region, which is from 400 nm thorough 800 nm. However, other wavelengths may also be used. In the exemplary imaging system 300, the light can be directly guided or otherwise provided into a fiber 372, which can be called an illumination fiber. The illumination fiber 372 can be connected to the FORJ 330, and further guided to (and/or associated with) another illumination fiber 310, which is connected to the FORJ 330 within a sheath 320. At the end of the illumination fiber 310, the exemplary SEE probe 302 can be attached. The light scattered back from an object or sample (e.g., tissue) can be collected by the probe 302 and guided to a detection fiber 312. The detection fiber 312 can be connected to another detection fiber 382 via the FORJ 330. The detection fiber 382 can be connected to the detector/spectrometer 380 via a collimating optical 384. The detector/spectrometer 380 can detect the intensity of selected wavelength. This exemplary function of detecting the selected wavelength can be performed by the spectrometer. By mechanically scanning the probe in a direction 328 perpendicular to the diffraction direction via a mechanical scanning unit contained within the FORJ 330, it is possible to obtain a two-dimensional image of the object. The mechanical scan can be performed by, e.g., Galvo scanner or motor to rotate the probe together with the illumination fiber 310 and the detection fiber 312. Computer 350 includes one or more microprocessors configured to control and operate the various parts of system 300, and executes computer-executable instructions (program code) to reconstruct images based on signals obtained from detector/spectrometer 330.

In some exemplary embodiments, instead of guiding the broadband light from light source 370 into the illumination fiber 372, the light can first be dispersed to predetermined wavelength(s) $\lambda_1, \lambda_2, \ldots, \lambda_N$. For example, the light with the wavelength $\lambda i$ ($1 \leq i \leq N$) can be input into the illumination fiber 372 in a multiplexed manner. The input light is provided through the junction (FORJ 330), illumination fiber 310, probe 302 to the sample; and collected via the probe 302, detection fiber 312, junction (FORJ 330), detection fiber 382, and guided to the detector/spectrometer 380. Optionally, in the case of imaging with light of individual wavelengths $\lambda i$, the detector/spectrometer 380 can be or include a simple light intensity detector such as photodetector because the input light has a wavelength of $\lambda i$. By changing i from 1 to N, it is possible to obtain the one-dimensional line image, by using a simple intensity photodetector or a line sensor. By mechanically scanning the line, it is possible to acquire the two-dimensional image of the object.

The FORJ 330 can be optional. One role of the optional junction (FORJ 330) can be to make the probe 302, including the illumination fiber 310 and the detection fiber 312, detachable. With this exemplary function, the probe 302 can be disposable and thus a sterile probe for human "in vivo" use can be provided every time an imaging operation is performed.

Various exemplary SEE probes as described and shown herein can deflect light along the reference axis, and facilitate forward viewing. The exemplary probe may be held stationary or it may be rotated, where the rotation of the probe is particularly useful for acquiring a two-dimensional front-view image as well as a color image.

For example, since the detection fiber 312 can be attached to the front-view type SEE probe, continuous rotation of the probe can cause the illumination fiber 310 and the detection fiber 312 to become tangled. Therefore, in some exemplary embodiments, it is possible that the probe can be rotated, e.g., +/−approximately 360 degrees back and forth. In other exemplary embodiments, the exemplary probe can be rotated +/−approximately 180 degrees back and forth. In further exemplary embodiments, other degrees of rotation can be used, such as, e.g., 90 degrees or 270 degrees of back and forth rotation.

According to various exemplary embodiments, a multi-cladding fiber can be utilized for both the illumination fiber 310 and the detection fiber 312. Multi-cladding fiber can act as if it has different core diameters depending on a light propagating direction. Thus, such multi-cladding fiber can be used as the illumination fiber and the detection fiber. If the multi-cladding fiber is connected to a "rotary junction," continuous rotation of the probe can be performed.

This exemplary imaging system 300 can be used with, for example, the exemplary probes as described in the various exemplary embodiments herein. The exemplary front-view SEE probes as described herein are categorized into two exemplary types. One type of probe can use an illumination fiber and a detection fiber. Another type of probe can use only one fiber, which may be, for example, a multi-cladding (double clad) fiber.

Certain aspects of the various embodiment(s) of the present invention can be realized by one or more computers that reads out and executes computer executable instructions (e.g., one or more programs) recorded on a transitory or non-transitory storage medium to perform the functions of one or more of the above-described embodiment(s) and/or that includes one or more circuits for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer system, for example, is part of or attached to the imaging processor and can obtain and modify information received from the imaging detector and an optional second detector. For example, the computer system can be used to process the three different orders of light and create a color image based on the images from the three different orders.

Thus, the detector/spectrometer 380 can be connected to computer 350 which includes an imaging processor and one or more display units connected to the imaging processor via a high definition multimedia interface (HDMI). Optionally, a separate image server is another computer unit connected to the processor connected via an Ethernet cable or a wireless access point.

Figure 24:
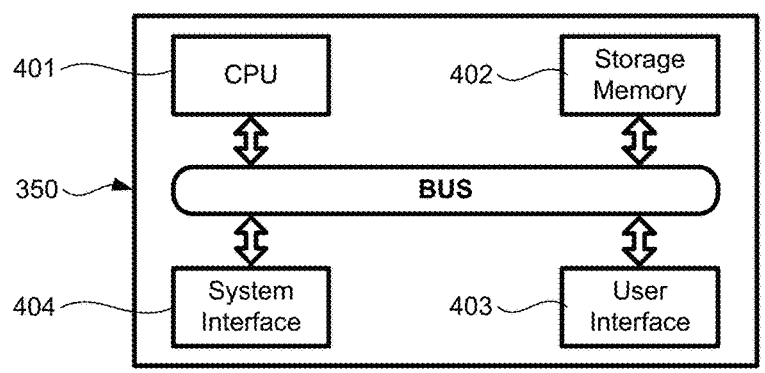
FIG. 24 shows a schematic of an exemplary imaging console.

FIG. 24 a schematic block diagram of a control and processing system applicable to the various embodiments of a SEE probe described herein. As shown in FIG. 24, the computer control system is representative of computer 350 shown in FIG. 23. In FIG. 24, the computer 350 includes central processing unit (CPU) 401, a storage memory (RAM) 402, a user input/output (I/O) interface 403, and a system interface 404. The computer 350 described by FIG. 24 can issue a command that can be transmitted to the imaging system 300 via a user interface unit/arrangement 403. A touch panel screen can be included as part of the user interface unit/imaging processor, but key board, mouse, joy-stick, ball controller, and foot pedal can also be included. The user can cause a command to be initiated to observe inside a lumen of the human body through the exemplary front-view SEE probe using the user interface unit/imaging processor. For example, when the user inputs a command via the user interface 403, the command is transmitted to the central processing unit CPU 401 for execution thereby causing the CPU to issue a command via the system interface 404 to one or more of the light source 370, detector/spectrometer 380 or FORJ 330.

The CPU 401 is comprised of one or more processors (microprocessors) configured to read and perform computer-executable instructions stored in the storage memory 402. The computer-executable instructions may include program code for the performance of the novel processes, methods and/or calculations disclosed herein.

The computer 350 functions as imaging processor that can be programmed to apply exemplary image processing such as noise reduction, coordinate distortion correction, contrast enhancement and so on. After or even during the image processing is performed, the data can be transmitted from the imaging processor to a display (not shown). A liquid crystal display (LCD) can be the display. The display can display, for example, the individual images obtained from a single color or a composite color image according to the various exemplary embodiments of the present disclosure. The display can also display other information than the image, such as the date of observation, what part of the human body is observed, the patient's name, operator's name and so on.

The CPU 401 is configured to read and perform computer-executable instructions stored in the Storage/RAM 402. The computer-executable instructions may include those for the performance of the methods and/or calculations described herein. For example, CPU 401 may calculate the angular momentum or speed of rotation of the SEE probe, and can use that information (rotation speed or angular momentum) to operate the FORJ. In this manner, computer 350 can obtain a new set of images where their angular positions are corrected. Storage/RAM 402 includes one or more computer readable and/or writable media, and may include, for example, a magnetic disc (e.g., a hard disk), an optical disc (e.g., a DVD, a Blu-ray), a magneto-optical disk, semiconductor memory (e.g., a non-volatile memory card, flash memory, a solid state drive, SRAM, DRAM), an EPROM, an EEPROM, etc. Storage/RAM 402 may store computer-readable data and/or computer-executable instructions. The components of the processor may communicate via a bus.

The system I/O interface 404 provides communication interfaces to input and output devices, which may include a keyboard, a display, a mouse, a printing device, a touch screen, a light pen, an optical storage device, a scanner, a microphone, a camera, a drive, communication cable and a network (either wired or wireless).

The system I/O interface 404 also provides communication interfaces to input and output devices. The detector may include, for example a photomultiplier tube (PMT), a photodiode, an avalanche photodiode detector (APD), a charge-coupled device (CCD), multi-pixel photon counters (MPPC), or other. Also, the function of detector may be realized by computer executable instructions (e.g., one or more programs) recorded on a Storage/RAM 402.

In an exemplary operation, the user can placed the exemplary SEE probe into a sheath, and then can insert such arrangement/configuration into a predetermined position of a human body. The sheath alone may be inserted into the human body in advance, and it is possible to insert the SEE probe into the sheath after sheath insertion. The exemplary probe can be used to observe inside human body and works as endoscope such as arthroscopy, bronchoscope, sinuscope, vascular endoscope and so on.

Definitions

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The term "substantially", as used herein means that, within fabrication parameters and/or measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

The foregoing merely illustrates the principles of the disclosure. Various modifications and alterations to the described exemplary embodiments will be apparent to those skilled in the art in view of the teachings herein. Indeed, the arrangements, systems and methods according to the exemplary embodiments of the present disclosure can be used with any SEE system or other imaging systems, and for example with those described in U.S. Pat. Nos. 6,341,036; 7,796,270; 7,843,572; 7,859,679; 8,045,177; 8,145,018; 8,780,176; and 8,812,087; and U.S. Patent Application Nos. 2008/0013960 and 2011/0237892; and PCT publications WO2015/116951 and WO2015116939, the disclosures of which are incorporated by reference herein in their entireties.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A probe having an optical axis, comprising:
   a light guiding component; a light focusing component; and a grating component, arranged in this order along the probe optical axis,
   wherein the probe is configured for guiding a light from the light guiding component, through the light focusing component and to the grating component in the direction of the probe optical axis, and then forwarding a spectrally dispersed light from the grating component towards a sample with no intermediate reflections between the light guiding component and the grating component, and wherein the grating component is configured to forward at least one spectral component of the spectrally dispersed light substantially parallel to the probe optical axis.

2. The probe of claim 1, wherein the grating component comprises a triangular grating.

3. The probe of claim 1, wherein the probe is a spectrally encoded endoscopy (SEE) probe.

4. The probe of claim 1, wherein the grating component comprises a triangular grating having a first surface substantially perpendicular to the direction of the probe optical axis, and a second surface substantially parallel to the direction of the probe optical axis, wherein the grating component satisfies the following equations:

$$\sin\theta_i = \frac{-mG\lambda_0}{n_i - n_d}$$

$$\sin\theta_d = \frac{n_i mG(\lambda - \lambda_0) - n_d mG\lambda}{(n_i - n_d)n_d}$$

where m is the grating component diffraction order, G is the grating component spatial frequency, $\lambda$ is a wavelength of light incident on the grating component, $\lambda_0$ is a specific wavelength of a light diffracted by the grating component, $n_i$ and $n_d$ are refractive indexes of the incident light and a diffracted light respectively, $\theta_i$ is the incidence angle of the incident light on the grating component and $\theta_d$ is the diffraction angle of the light diffracted by the grating component.

5. The probe of claim 1, wherein a light diffracted from the grating component having a wavelength of between 400 nm and 1000 nm has substantially no $0^{th}$ order component.

6. The probe of claim 1, wherein the grating component comprises a first refractive surface substantially perpendicular to the direction of the probe optical axis.

7. The probe of claim 6, wherein the grating component comprises a second refractive surface substantially parallel to the direction of the probe optical axis.

8. The probe of claim 1, wherein the grating component is a transmissive grating configured to enhance one or more of transmitted orders of diffracted light.

9. The probe of claim 8, wherein the grating component is configured to enhance the $4^{th}$, $5^{th}$, and $6^{th}$ orders of diffracted light.

10. The probe of claim 8, wherein the grating component has a staircase design.

11. The probe of claim 1, wherein the light focusing component is a gradient index (GRIN) lens or a ball lens.

12. The probe of claim 1, wherein the probe is configured for guiding and diffracting a visible light and wherein the grating component is configured to diffract the visible light such that there is at least one wavelength within the visible light having an incidence angle $\theta_i$, and a diffraction angle $\theta_d$ such that $\theta_i = \theta_d$.

13. The probe of claim 1, wherein the probe is configured for guiding and diffracting visible light, wherein the grating component is configured to diffract the visible light such that the shortest wavelength of the visible light propagates from the grating component substantially parallel to the probe optical axis.

14. The probe of claim 1, wherein the grating component is configured to minimize reflection of light incident on the grating component by destructive interference upon reflection.

15. The probe of claim 1, further comprising:

a reflective surface that is optically flat arranged on a side surface of the grating component, wherein the grating component and the reflective surface are configured to guide a reflected $0^{th}$ order light back onto the grating component.

16. The probe of claim 1, further comprising a detection fiber positioned and configured to receive at least one reflected light from the sample.

17. The probe of claim 1, further comprising at least two detection fibers positioned and configured to receive reflected light from the sample, wherein at least one detection fiber is positioned and configured to receive at least one reflected light from a position on the sample substantially along the probe optical axis and at least one detection fiber is positioned and configured to receive at least one reflected light from a position on the sample substantially angled with respect to the probe optical axis.

18. The probe of claim 17, further comprising a second grating component arranged on a side surface of the grating component.

19. The probe of claim 18, wherein the second grating component is positioned and configured to diffract a $0^{th}$ order light reflected by the grating component, and wherein the detection fiber positioned and configured to receive at least one reflected light from a position on the sample substantially angled with respect to the probe optical axis comprises a grating at the distal end thereof.

20. The probe of claim 1, wherein the grating period $\Lambda$ is between 0.75 and 1.25 μm.

21. The probe of claim 1, wherein the grating period $\Lambda$ is at least 1.5 μm.

22. The probe of claim 1, wherein the half field of view (FOV) angle of the probe is between 30 and 80 degrees for diffracted light having a wavelength between 400 and 800 nanometers, wherein the half FOV angle is defined as $\Delta\theta = \theta_d - \theta_i$, where $\theta_i$ is the incidence angle of the light incident on the grating component and $\theta_d$ is the diffraction angle of the light diffracted by the grating component.

23. A system comprising
a light guiding component;
a light focusing component;
a grating component,
a rotary element,
one or more detection fibers,
one or more detectors, and
one or more processors configured to processes light from multiple orders of diffracted light detected by the one or more detectors, and to form a single color image or a multicolor image based on that processed light, wherein the light guiding component, light focusing component and grating component are arranged along an optical axis to form a probe configured for guiding a light from the light guiding component, through the light focusing component and to the grating component in the direction of the probe optical axis, and then forwarding a spectrally dispersed light from the grating component towards a sample, wherein the grating component is configured to forward at least one spectral component of the spectrally dispersed light substantially parallel to the probe optical axis, and wherein the one or more detectors are configured to detect light of multiple orders of diffracted light reflected from the sample.

24. The system according to claim 23, wherein the probe is configured to guide the light from the light guiding component, through the light focusing component and to the grating component with no intermediate reflections between the light guiding component and the grating component.

25. The system according to claim 23, wherein the grating component comprises a transmissive grating having a first surface substantially parallel to the probe optical axis and a second surface at an angle with respect to the probe optical axis.

26. The probe of claim 1, wherein the grating component comprises a triangular grating having a first surface substantially parallel to the direction of the probe optical axis, and a second surface at an angle with respect to the direction of the probe optical axis.

* * * * *